US008540723B2

(12) United States Patent
Shadduck et al.

(10) Patent No.: US 8,540,723 B2
(45) Date of Patent: Sep. 24, 2013

(54) MEDICAL SYSTEM AND METHOD OF USE

(75) Inventors: John H. Shadduck, Tiburon, CA (US); Andrew Kohm, San Mateo, CA (US)

(73) Assignee: DFINE, Inc., San Jose, CA (US)

(*) Notice: Subject to any disclaimer, the term of this patent is extended or adjusted under 35 U.S.C. 154(b) by 563 days.

(21) Appl. No.: 12/759,573

(22) Filed: Apr. 13, 2010

(65) Prior Publication Data

US 2010/0262152 A1   Oct. 14, 2010

Related U.S. Application Data

(60) Provisional application No. 61/212,622, filed on Apr. 14, 2009.

(51) Int. Cl.
| | |
|---|---|
| *A61B 17/58* | (2006.01) |
| *A61B 17/60* | (2006.01) |
| *A61F 2/00* | (2006.01) |
| *B01F 13/06* | (2006.01) |
| *B01F 15/00* | (2006.01) |
| *B01F 15/06* | (2006.01) |

(52) U.S. Cl.
USPC ............. 606/94; 366/139; 366/142; 366/145; 366/146; 366/163.1

(58) Field of Classification Search
USPC .............. 366/139, 144, 145, 146, 163.1, 142; 606/92–94
See application file for complete search history.

(56) References Cited

U.S. PATENT DOCUMENTS

| | | | |
|---|---|---|---|
| 3,349,840 A | 10/1967 | Tope et al. | |
| 3,376,999 A | 4/1968 | De Hart et al. | |
| 3,739,947 A | 6/1973 | Baumann et al. | |
| 4,377,168 A | 3/1983 | Rzasa et al. | |
| 4,416,995 A * | 11/1983 | Amaral .................... 435/287.3 |
| 5,051,482 A | 9/1991 | Tepic | |
| 5,130,950 A | 7/1992 | Orban et al. | |
| 5,145,250 A | 9/1992 | Planck et al. | |
| 5,531,683 A | 7/1996 | Kriesel et al. | |
| 5,542,928 A | 8/1996 | Evans et al. | |
| 5,688,252 A | 11/1997 | Matsuda et al. | |
| 5,713,857 A | 2/1998 | Grimard et al. | |
| 5,788,711 A | 8/1998 | Lehner et al. | |
| 5,865,798 A | 2/1999 | Grimard et al. | |
| 5,899,881 A | 5/1999 | Grimard et al. | |
| 6,075,067 A | 6/2000 | Lidgren | |
| 6,120,174 A | 9/2000 | Hoag et al. | |
| 6,122,549 A | 9/2000 | Sharkey et al. | |
| 6,264,659 B1 | 7/2001 | Ross et al. | |
| 6,312,149 B1 | 11/2001 | Sjovall et al. | |
| 6,575,930 B1 | 6/2003 | Trombley, III et al. | |
| 6,709,149 B1 | 3/2004 | Tepic | |
| 6,736,537 B2 | 5/2004 | Coffeen et al. | |

(Continued)

FOREIGN PATENT DOCUMENTS

WO    WO 02/064062    8/2002

*Primary Examiner* — Anu Ramana
(74) *Attorney, Agent, or Firm* — Knobbe Martens Olson & Bear LLP

(57) ABSTRACT

A medical system and method can used to treat a bone. The system and method can include the preparation of bone cement to be used in the treatment. A non-liquid component and a liquid component can be combined to form a bone cement. A vacuum system can be used to saturate the non-liquid component with the liquid component. The bone cement and/or components can be heated and/or cooled.

19 Claims, 17 Drawing Sheets

(56) References Cited

U.S. PATENT DOCUMENTS

| | | |
|---|---|---|
| 6,832,988 B2 | 12/2004 | Sprout |
| 6,964,667 B2 | 11/2005 | Shaolian et al. |
| 6,979,352 B2 | 12/2005 | Reynolds |
| 7,008,433 B2 | 3/2006 | Voellmicke et al. |
| 7,048,720 B1 | 5/2006 | Thorne, Jr. et al. |
| 7,048,743 B2 | 5/2006 | Miller et al. |
| 7,073,936 B1 | 7/2006 | Jonsson |
| 7,160,020 B2 | 1/2007 | Sand |
| 7,259,210 B2 | 8/2007 | Puckett et al. |
| 7,559,932 B2 | 7/2009 | Truckai et al. |
| 7,678,116 B2 | 3/2010 | Truckai et al. |
| 8,066,712 B2 | 11/2011 | Truckai et al. |
| 2002/0068974 A1 | 6/2002 | Kuslich et al. |
| 2004/0180986 A1 | 9/2004 | Bellare et al. |
| 2006/0000284 A1 | 1/2006 | Sherman et al. |
| 2006/0052794 A1 | 3/2006 | McGill et al. |
| 2006/0079834 A1 | 4/2006 | Tennican et al. |
| 2008/0188858 A1 | 8/2008 | Luzzi et al. |
| 2009/0062808 A1 | 3/2009 | Wolf, II |
| 2009/0093550 A1 | 4/2009 | Rolfes et al. |
| 2009/0093818 A1* | 4/2009 | Baroud .................... 606/93 |
| 2009/0171362 A1 | 7/2009 | Schaeffer |
| 2009/0281549 A1 | 11/2009 | Dixon |
| 2009/0292290 A1 | 11/2009 | Truckai et al. |
| 2010/0091606 A1 | 4/2010 | Kwan et al. |
| 2010/0110436 A1 | 5/2010 | Chandler et al. |
| 2010/0168271 A1 | 7/2010 | Beyar et al. |

* cited by examiner

150A PLACE POWDER COMPONENT OF CURABLE BONE CEMENT UNDER CONTROLLED COMPACTION INTO AN INTERIOR SPACE OF CEMENT-CARRYING MEMBER

150B INTRODUCE LIQUID MONOMER COMPONENT OF CURABLE BONE CEMENT INTO FIRST END OF INTERIOR SPACE OF CEMENT-CARRYING MEMBER

150C APPLY NEGATIVE PRESSURE TO SECOND END OF INTERIOR SPACE OF CEMENT-CARRYING MEMBER TO THEREBY INFUSE LIQUID MONOMER THROUGH POWDER

150D CONTROL VOLUME OF MONOMER WITHIN POWDER WITH CONTROLLED POROSITY FILTER INTERMEDIATE THE NEGATIVE PRESSURE SOURCE AND INTERIOR SPACE

150E UTILIZE FORCE APPLICATION MECHANISM TO EJECT BONE CEMENT MIXTURE FROM THE CEMENT-CARRYING MEMBER INTO PATIENT'S BONE

*FIG. 4*

380A
PLACE POWDER COMPONENT OF CURABLE BONE CEMENT UNDER CONTROLLED COMPACTION IN < 5CC INTERIOR SPACES OF MULTIPLE CEMENT-CARRYING MEMBERS

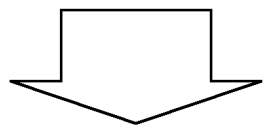

380B
INTRODUCE LIQUID MONOMER COMPONENT OF CURABLE BONE CEMENT INTO FIRST END OF INTERIOR SPACES OF CEMENT-CARRYING MEMBERS

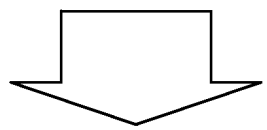

380C
UTILIZE COMPUTER-CONTROLLED APPLICATION OF NEGATIVE PRESSURE TO SECOND ENDS OF INTERIOR SPACES OF CEMENT-CARRYING MEMBERS TO INFUSE MONOMER THROUGH POWDER

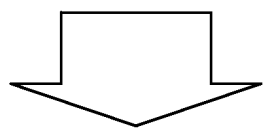

380D
UTILIZE FORCE APPLICATION MECHANISM TO SEQUENTIALLY EJECT BONE CEMENT MIXTURE FROM THE CEMENT-CARRYING MEMBER INTO PATIENT'S BONE

*FIG. 7*

480A
PLACE POWDER COMPONENT OF CURABLE BONE CEMENT UNDER CONTROLLED COMPACTION IN INTERIOR SPACE OF CEMENT-CARRYING MEMBER(S)

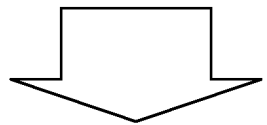

480B
PRE-HEAT THE POWDER COMPONENT TO PREDETERMINED TEMPERATURE IN RANGE OF 30°C TO 60°C; AND/OR PRE-HEAT LIQUID MONOMER COMPONENT

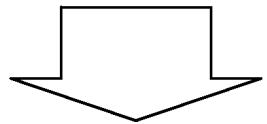

480C
COMBINE POWDER COMPONENT AND MONOMER COMPONENT TO PROVIDE CURABLE BONE CEMENT

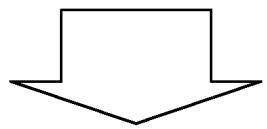

480D
UTILIZE FORCE APPLICATION MECHANISM TO EJECT BONE CEMENT MIXTURE FROM THE CEMENT-CARRYING MEMBER(S) INTO PATIENT'S BONE

*FIG. 11*

580A — PLACE POWDER COMPONENT OF CURABLE BONE CEMENT UNDER CONTROLLED COMPACTION IN INTERIOR SPACE OF CEMENT-CARRYING MEMBER(S)

580B — PRE-HEAT THE POWDER COMPONENT TO PREDETERMINED TEMPERATURE IN RANGE OF 30°C TO 60°C; AND/OR PRE-HEAT LIQUID MONOMER COMPONENT

580C — COMBINE POWDER COMPONENT AND MONOMER COMPONENT TO PROVIDE CURABLE BONE CEMENT

580D — UTILIZE COMPUTER-CONTROLLED COOLING MECHANISM TO COOL BONE CEMENT MIXTURE IN INTERIOR SPACE OF THE CEMENT-CARRYING MEMBER(S)

580E — UTILIZE FORCE APPLICATION MECHANISM TO EJECT BONE CEMENT MIXTURE FROM THE CEMENT-CARRYING MEMBER(S) INTO PATIENT'S BONE

*FIG. 13*

MEDICAL SYSTEM AND METHOD OF USE

CROSS-REFERENCE TO RELATED APPLICATIONS

This application claims the benefit of priority under 35 U.S.C. §119(e) of U.S. Provisional Application No. 61/212,622, filed Apr. 14, 2009. This application is related to the following U.S. patent application Ser. No. 11/209,035 filed Aug. 22, 2005, Ser. No. 12/427,531 filed Apr. 21, 2009, Ser. No. 12/345,937 filed Dec. 30, 2008, and Ser. No. 12/578,163 filed Oct. 13, 2009; and is related to Provisional Application Nos. 60/842,805 filed Sep. 7, 2006 and 60/713,521 filed Sep. 1, 2005. The entire contents of all of the above applications are hereby incorporated by reference and should be considered a part of this specification.

BACKGROUND OF THE INVENTION

1. Field of the Invention

Embodiments of the present disclosure relate to bone cement injection systems, and in some embodiments provide a system for controlling the viscosity of injected bone cement to prevent extravasation.

2. Description of the Related Art

Osteoporotic fractures are prevalent in the elderly, with an annual estimate of 1.5 million fractures in the United States alone. These include 750,000 vertebral compression fractures (VCFs) and 250,000 hip fractures. The annual cost of osteoporotic fractures in the United States has been estimated at $13.8 billion. The prevalence of VCFs in women age 50 and older has been estimated at 26%. The prevalence increases with age, reaching 40% among 80-year-old women. Medical advances aimed at slowing or arresting bone loss from aging have not provided solutions to this problem. Further, the population affected will grow steadily as life expectancy increases. Osteoporosis affects the entire skeleton but most commonly causes fractures in the spine and hip. Spinal or vertebral fractures also cause other serious side effects, with patients suffering from loss of height, deformity and persistent pain which can significantly impair mobility and quality of life. Fracture pain usually lasts 4 to 6 weeks, with intense pain at the fracture site. Chronic pain often occurs when one vertebral level is greatly collapsed or multiple levels are collapsed.

Postmenopausal women are predisposed to fractures, such as in the vertebrae, due to a decrease in bone mineral density that accompanies postmenopausal osteoporosis. Osteoporosis is a pathologic state that literally means "porous bones". Skeletal bones are made up of a thick cortical shell and a strong inner meshwork, or cancellous bone, of collagen, calcium salts and other minerals. Cancellous bone is similar to a honeycomb, with blood vessels and bone marrow in the spaces. Osteoporosis describes a condition of decreased bone mass that leads to fragile bones which are at an increased risk for fractures. In an osteoporosis bone, the sponge-like cancellous bone has pores or voids that increase in dimension making the bone very fragile. In young, healthy bone tissue, bone breakdown occurs continually as the result of osteoclast activity, but the breakdown is balanced by new bone formation by osteoblasts. In an elderly patient, bone resorption can surpass bone formation thus resulting in deterioration of bone density. Osteoporosis occurs largely without symptoms until a fracture occurs.

Vertebroplasty and kyphoplasty are recently developed techniques for treating vertebral compression fractures. Percutaneous vertebroplasty was first reported by a French group in 1987 for the treatment of painful hemangiomas. In the 1990's, percutaneous vertebroplasty was extended to indications including osteoporotic vertebral compression fractures, traumatic compression fractures, and painful vertebral metastasis. Vertebroplasty is the percutaneous injection of PMMA (polymethylmethacrylate) into a fractured vertebral body via a trocar and cannula. The targeted vertebrae are identified under fluoroscopy. A needle is introduced into the vertebrae body under fluoroscopic control, to allow direct visualization. A bilateral transpedicular (through the pedicle of the vertebrae) approach is typical but the procedure can be done unilaterally. The bilateral transpedicular approach allows for more uniform PMMA infill of the vertebra.

In a bilateral approach, approximately 1 to 4 ml of PMMA is used on each side of the vertebra. Since the PMMA needs to be forced into the cancellous bone, the techniques require high pressures and fairly low viscosity cement. Since the cortical bone of the targeted vertebra may have a recent fracture, there is the potential of PMMA leakage. The PMMA cement contains radiopaque materials so that when injected under live fluoroscopy, cement localization and leakage can be observed. The visualization of PMMA injection and extravasation are critical to the technique—and the physician terminates PMMA injection when leakage is evident. The cement is injected using syringes to allow the physician manual control of injection pressure.

Balloon kyphoplasty is a modification of percutaneous vertebroplasty. Balloon kyphoplasty involves a preliminary step comprising the percutaneous placement of an inflatable balloon tamp in the vertebral body. Inflation of the balloon creates a cavity in the bone prior to cement injection. In balloon kyphoplasty, the PMMA cement can be injected at a lower pressure into the collapsed vertebra since a cavity exists, as compared to conventional vertebroplasty. More recently, other forms of kyphoplasty have been developed in which various tools are used to create a pathway or cavity into which the bone cement is then injected.

The principal indications for any form of vertebroplasty are osteoporotic vertebral collapse with debilitating pain. Radiography and computed tomography must be performed in the days preceding treatment to determine the extent of vertebral collapse, the presence of epidural or foraminal stenosis caused by bone fragment retropulsion, the presence of cortical destruction or fracture and the visibility and degree of involvement of the pedicles.

Leakage of PMMA during vertebroplasty can result in very serious complications including compression of adjacent structures that necessitate emergency decompressive surgery. See Groen, R. et al., "Anatomical and Pathological Considerations in Percutaneous Vertebroplasty and Kyphoplasty: A Reappraisal of the Vertebral Venous System," Spine Vol. 29, No. 13, pp 1465-1471, 2004. Leakage or extravasation of PMMA is a critical issue and can be divided into paravertebral leakage, venous infiltration, epidural leakage and intradiscal leakage. The exothermic reaction of PMMA carries potential catastrophic consequences if thermal damage were to extend to the dural sac, cord, and nerve roots. Surgical evacuation of leaked cement in the spinal canal has been reported. It has been found that leakage of PMMA is related to various clinical factors such as the vertebral compression pattern, and the extent of the cortical fracture, bone mineral density, the interval from injury to operation, the amount of PMMA injected and the location of the injector tip. In one recent study, close to 50% of vertebroplasty cases resulted in leakage of PMMA from the vertebral bodies. See Hyun-Woo Do et al., "The Analysis of Polymethylmethacrylate Leakage after Vertebroplasty for Vertebral Body Compression Fractures," J. of Korean Neurosurg. Soc., Vol. 35, No. 5 (May/2004), pp 478-82, (http://www.jkns.or.kr/htm/abstract.asp?no=0042004086).

Another recent study was directed to the incidence of new VCFs adjacent to the vertebral bodies that were initially treated. Vertebroplasty patients often return with new pain caused by a new vertebral body fracture. Leakage of cement into an adjacent disc space during vertebroplasty increases the risk of a new fracture of adjacent vertebral bodies. See Am. J. Neuroradiol., 2004 February; 25(2):175-80. The study found that 58% of vertebral bodies adjacent to a disc with cement leakage fractured during the follow-up period compared with 12% of vertebral bodies adjacent to a disc without cement leakage.

Another life-threatening complication of vertebroplasty is pulmonary embolism. See Bernhard, J. et al., "Asymptomatic Diffuse Pulmonary Embolism Caused by Acrylic Cement: An Unusual Complication of Percutaneous Vertebroplasty," Ann. Rheum. Dis., 62:85-86, 2003. The vapors from PMMA preparation and injection also are cause for concern. See Kirby, B. et al., "Acute Bronchospasm Due to Exposure to Polymethylmethacrylate Vapors During Percutaneous Vertebroplasty," Am. J. Roentgenol., 180:543-544, 2003.

SUMMARY OF THE INVENTION

There is a general need to provide bone cements and methods for use in treatment of vertebral compression fractures that provide a greater degree of control over introduction of cement and that provide better outcomes. The present invention meets this need and provides several other advantages in a novel and nonobvious manner.

Certain embodiments provide bone cement injectors and control systems that allow for vertebroplasty procedures that inject cement having a substantially constant viscosity over an extended cement injection interval.

A computer controller can be provided to control cement flow parameters in the injector and energy delivery parameters for selectively accelerating polymerization of bone cement before the cement contacts the patient's body.

In some embodiments, a system is provided for preparing bone cement. The system can comprise a base and a negative pressure source. The base can be configured to couple to one or more elongate members, where at least one of the elongate members can be configured to hold a non-liquid polymer component in a lumen thereof and to receive a liquid monomer component therein for saturation of the non-liquid polymer component by the liquid monomer component to form a curable bone cement. The negative pressure source can be configured for detachable communication with the base to draw the liquid monomer component into the non-liquid powder component. Further, the base can include one or more pathways that communicate the lumen of the one or more elongate members and the negative pressure source.

According to certain embodiments, the system can further include one or more valves for selectively coupling the negative pressure source to particular elongate members of the plurality of elongate members. Additionally, a computer controller can be provided to control the plurality of valves, for example, so that the valves can be opened or closed substantially simultaneously or a selected time intervals. The computer controller may also include a signal system to indicate to a user when to use a particular elongate member in a particular medical treatment or when to add liquid monomer component to a particular elongate member.

The system can further include one or more of: a pressure regulator for regulating the pressure of the negative pressure source applied to draw the liquid polymer into the elongate member; a funnel member for coupling to an end of the elongate members; a cement ejection mechanism configured to couple to one of the elongate members and to eject bone cement from the elongated member into bone; a computer controller operatively coupled to the negative pressure source for controlling a negative pressure level applied to each elongate member; a heating and/or cooling mechanism for respectively heating or cooling the plurality of elongate members and the component or bone cement contained therein; and a computer controller for controlling either or both of the heating and cooling mechanisms.

In some embodiments, a system for preparing bone cement can include a structure for receiving a plurality of bone cement preparation members. The plurality of bone cement preparation members can be configured to receive a liquid monomer component and a non-liquid polymer component, the combination of which forms a curable bone cement within the plurality of bone cement preparation members. The structure can include a plurality of channels and a plurality of temperature regulating assemblies. The plurality of channels can be configured to connect an end of each of the plurality of bone cement preparation members to a negative pressure source. Each of the plurality of temperature regulating assemblies can be for heating or cooling one of the plurality of bone cement preparation members. The system may further include a computer controller for controlling the amount of heat or cooling provided to the plurality of bone cement preparation members to heat or cool one of the components or the curable bone cement therein.

According to some embodiments each of the temperature regulating assemblies can comprise a sleeve configured to receive and surround one of the plurality of bone cement preparation members. The temperature regulating assemblies can further include a seal to seal an access opening of the temperature regulating assembly once a bone cement preparation member has been placed inside the temperature regulating assembly. An air flow passage can exist between an interior surface of the temperature regulating assembly and an exterior surface of the bone cement preparation member. The temperature regulating assembly can have an input and output port in fluid communication with the air flow passage. A heating or cooling source can generate a hot or cold flow of gas or liquid to enter the input port and exit the output port.

A method of treating a bone, according to some embodiments can include the steps of: (a) providing a first liquid component and a second non-liquid component of a curable bone cement, (b) heating one or more of the cement components with a heating system prior to combining the components, wherein the heating system controls the temperature of the one or more components within a range of 1° C. on either side of a predetermined temperature, and (c) applying a partial vacuum to the non-liquid component to saturate the non-liquid component with the liquid component while maintaining particles of the non-liquid component in a fixed relationship within a container.

In some embodiments of the method, the non-liquid component is carried within a plurality of elongated sleeves. The heating system can include at least one of an inductive heating system, a resistive heating system, a light energy heating system, a heated air or gas circulating system, an RF heating system, a microwave heating system, a magnetic heating system, and a heated liquid circulating system. The heating system may also be configured to convectively heat the bone cement component, heat a member that contains the bone cement component, or heat a structure or space that is adjacent a member that contains the bone cement component.

According to certain embodiments, a method of treating a patient can comprise placing each of a plurality of containers of a non-liquid polymer powder component within a temperature regulating sleeve, placing a container of a liquid monomer component into a temperature regulating sleeve, heating the liquid monomer component via the temperature regulating sleeve, and pouring the heated liquid monomer component into at least two of the containers of non-liquid polymer powder component. The method may further include applying suction to the least two containers of non-liquid polymer powder component to saturate the powder with the liquid so that the non-liquid polymer powder component and the liquid monomer component form a bone cement and thus at least two containers contain bone cement and removing a first container of bone cement from the temperature regulating sleeve and ejecting the bone cement into a bone.

In some embodiments, the method may further include the step cooling the at least one other container of bone cement while the first container is used to eject bone cement into the bone. In addition, removing the at least one other container of bone cement and ejecting the bone cement into the bone. The method can further include heating the at least one other container of bone cement after cooling and just prior to removing. In some embodiments, the method can further comprise heating the non-liquid polymer powder component.

These and other objects of the present invention will become readily apparent upon further review of the following drawings and specification.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

FIG. 4 is a block diagram of a method for utilizing the system of FIGS. 1 and/or 3.

FIG. 7 is a block diagram of a method for utilizing the system of FIGS. 5, 6A and/or 6B.

FIG. 11 is a block diagram of a method for utilizing the system of FIG. 8.

FIG. 13 is a block diagram of a method for utilizing the system of FIG. 12.

DETAILED DESCRIPTION OF THE PREFERRED EMBODIMENTS

Figure 1:
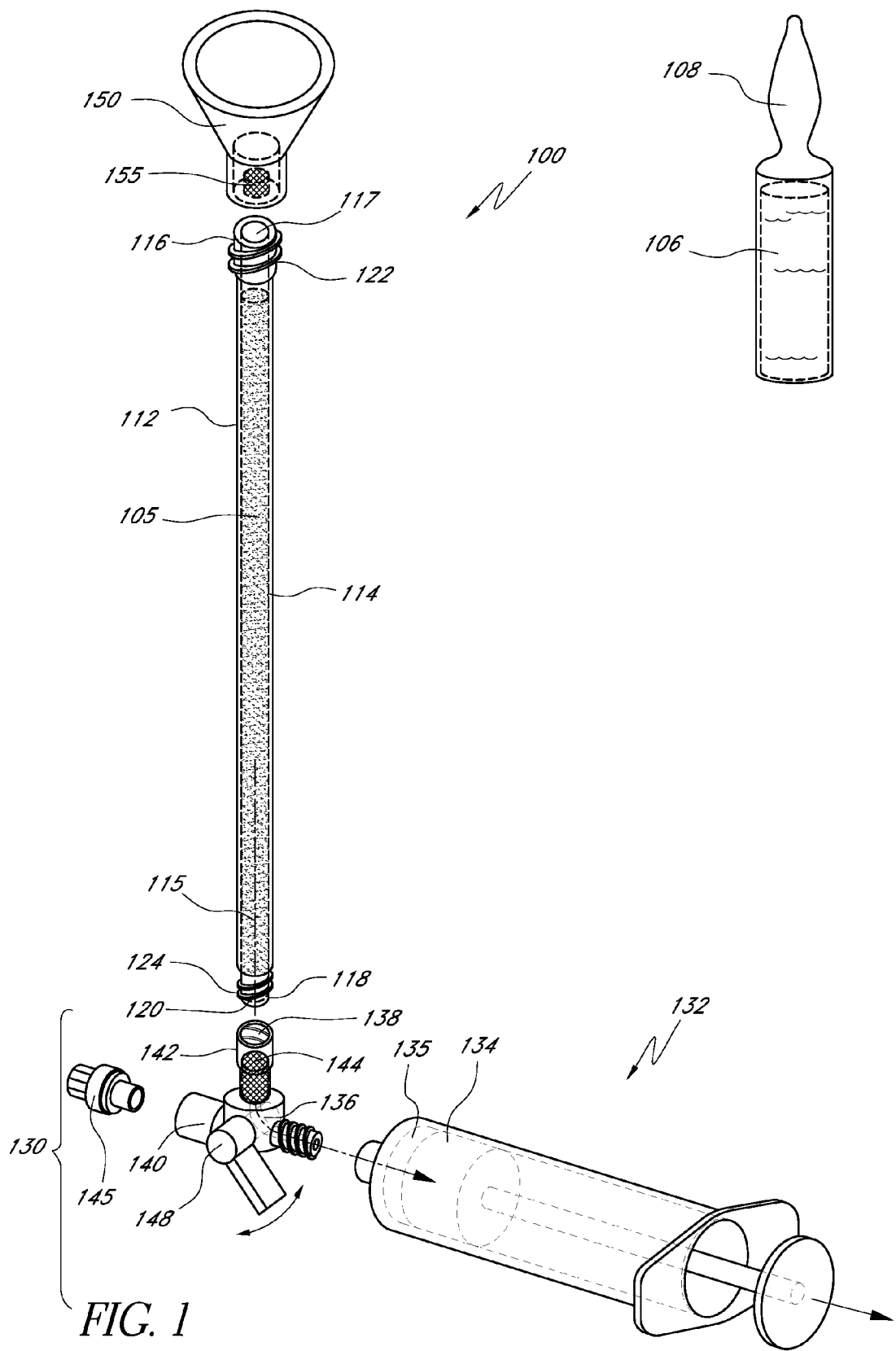
FIG. 1 is a perspective view of a system for bone cement preparation by vacuum saturation mixing of a polymer powder with a liquid monomer in accordance with some embodiments.

For purposes of understanding the principles of the invention, reference will now be made to the embodiments illustrated in the drawings and the accompanying text. As background, a vertebroplasty procedure using a bone cement injection system could insert parts of the system(s) described herein through a pedicle of a vertebra, or in a parapedicular approach, for accessing the osteoporotic cancellous bone. As an example, the bone cement delivery assembly or ejection mechanism shown in U.S. publication no. 2008/0249530 at FIGS. 1-2 and 9-16 could be used. U.S. publication no. 2008/0249530, published Oct. 9, 2008 is incorporated herein by reference and made a part of this specification, in particular, FIGS. 1-2 and 9-16 and the accompanying description, such as paragraphs [0055], [0061]-[0063].

The initial aspects of the procedure can be similar to a conventional percutaneous vertebroplasty wherein the patient is placed in a prone position on an operating table. The patient is typically under conscious sedation, although general anesthesia is an alternative. The physician injects a local anesthetic (e.g., 1% Lidocaine) into the region overlying the targeted pedicle or pedicles as well as the periosteum of the pedicle(s). Thereafter, the physician can use a scalpel to make a 1 to 5 mm skin incision over each targeted pedicle. Thereafter, an introducer can be advanced through the pedicle into the anterior region of the vertebral body, which typically is the region of greatest compression and fracture. The physician can confirm the introducer path posterior to the pedicle, through the pedicle and within the vertebral body by antero-posterior and lateral X-Ray projection fluoroscopic views or by other methods. The introduction of infill material as described below can be imaged several times, or continuously, during the treatment depending on the imaging method.

Definitions

"Bone cement, bone fill or fill material, infill material or composition" includes its ordinary meaning and is defined as any material for infilling a bone that includes an in-situ hardenable material or that can be infused with a hardenable material. The fill material also can include other "fillers" such as filaments, microspheres, powders, granular elements, flakes, chips, tubules and the like, autograft or allograft materials, as well as other chemicals, pharmacological agents or other bioactive agents.

"Flowable material" includes its ordinary meaning and is defined as a material continuum that is unable to withstand a static shear stress and responds with an irrecoverable flow (a fluid)—unlike an elastic material or elastomer that responds to shear stress with a recoverable deformation. Flowable material includes fill material or composites that include a fluid (first) component and an elastic or inelastic material (second) component that responds to stress with a flow, no matter the proportions of the first and second component, and wherein the above shear test does not apply to the second component alone.

"Substantially" or "substantial" mean largely but not entirely. For example, substantially may mean about 50% to about 99.999%, about 80% to about 99.999% or about 90% to about 99.999%.

"Vertebroplasty" includes its ordinary meaning and means any procedure wherein fill material is delivered into the interior of a vertebra.

"Osteoplasty" includes its ordinary meaning and means any procedure wherein fill material is delivered into the interior of a bone.

In FIG. 1, a system 100 is illustrated that can be adapted for both bone cement preparation and cement injection in a vertebroplasty procedure. The system 100 can utilize a specialized formulation of a two-part PMMA bone cement, with a non-liquid polymer powder component 105 and a liquid monomer component 106 (typically carried in vial 108) that post-mixing results in a curable bone cement 110, described further below.

In one embodiment shown in FIG. 1, the system 100 includes an elongated cement-carrying structure or sleeve 112. The sleeve 112 can be made of a metal or polymer with a thin wall that has an interior space or channel 114. The sleeve 112 can carry a volume of a non-liquid polymer powder component 105 of a bone cement. In some embodiments, the polymer powder component 105 is pre-packed within the sleeve 112. The sleeve 112 extends along axis 115 from a proximal end 116, with opening 117 into the interior space to a distal end 118 with an open termination 120 of the interior space 114. The proximal end 116 of the cement-carrying structure 112 can have a fitting such as a threaded or Luer fitting 122 for connecting a pressurization mechanism (described later) to the structure. The distal end 118 of the structure 112 can also have a fitting (e.g., a Luer fitting 124) for connecting a filter and/or vacuum source to the structure as will be described further below. These fittings can also be used for other purposes, such as to cap off the ends 116, 118 of the sleeve 112.

Still referring to FIG. 1, the cement-carrying sleeve 112, as shown, has an elongate configuration. The cross-section of the interior space 114, of some embodiments, can have a diameter of less than 5 mm, less than 4 mm or less than 3 mm. The length of the sleeve 112 along axis 115 can range from about 5 cm to 20 cm, and in one embodiment is 12 cm. The sleeve 112 can be a transparent biocompatible plastic or other material to allow viewing of the monomer saturation described below. The volume of the interior space 114 can carry from about 1 cc to 5 cc of the polymer powder component 105. In use in a vertebroplasty procedure, in one embodiment, one or more cement-carrying sleeves 112 can be used, as a treatment of a vertebral compression fracture can use from about 2 cc to 8 cc of bone cement.

The sleeve dimensions and cement volumes of a sleeve 112 can allow for rapid heating and/or cooling of the entire cross-section of polymer powder 105 or bone cement mixture 110 in the sleeve 112. It has been found that heating and/or cooling of a column of polymer powder, and particularly a monomer-saturated powder, can be best accomplished with a "uniform" temperature across the column when the cross section is less than about 5 mm. For example, in columns that have a greater cross sectional dimension than about 5 mm, the core of a polymerizing cement mixture may continue to have an unwanted elevated temperature due to the exothermic reaction, while the surface of the column may have a cooler temperature due to proximity to a cooling mechanism positioned about the exterior of the cement-carrying sleeve 112.

As can also be seen in FIG. 1, the system can include a negative pressure source or assembly 130. The negative pressure source 130 can be detachably coupled to sleeve 112 for suctioning the liquid monomer component 106 into and through the non-liquid polymer powder component 105 disposed in the sleeve 112. Saturation of the polymer powder 105 with the monomer 106 causes the cement to polymerize and set in a post-mixing (or post-saturation) time interval that is described further below.

In one embodiment, the negative pressure source 130 can have a syringe 132 with a lockable plunger assembly 134 that can be withdrawn to apply suction from syringe chamber 135 through channel 136 in body 140 that communicates with open termination 120 in sleeve 112 when connected together by cooperating fittings, such as threads 124 of sleeve 112 and the receiving threads 138 of the negative pressure source or assembly 130. In some embodiments the negative pressure source can include a gas cartridge with a negative pressure inside the cartridge, or can alternatively include any other vacuum line, evacuated cartridge or the like that can produce a vacuum. The negative pressure source or vacuum source 130 can be detachably coupled to the sleeve 112. This can be for suctioning the liquid monomer component 106 into and through the non-liquid polymer powder component 105 disposed in sleeve 112. The saturation of the polymer powder 105 with the monomer 106 can thus cause the biomaterial column to begin polymerization and set in post-mixing (or post-saturation) time intervals that are described further below.

The terms wetting and saturating are used interchangeably herein to describe the process of thoroughly (e.g., completely) exposing the non-liquid polymer powder component to the liquid monomer component, in other words to unite the two components to thereafter cause a polymerization reaction between at least two portions of the biomaterials.

In some embodiments, the vacuum source 130 can comprise a syringe. For example, the syringe can comprise a 20 cc to 60 cc syringe and more particularly a 30 cc syringe. It has been found that a 30 cc syringe can provide a negative pressure of −500 mmHg or greater. The size of the syringe and the amount of desired negative pressure of certain embodiments can vary greatly and can depend on many factors. These factors can include the amount of bone cement to be prepared, the cross-section and length of the mixing chamber and the volume and dimensions of the polymer beads. It has been found that high quality, commercially available 20 cc to 60 cc syringes can be actuated to provide about a negative pressure of −250 mmHg to −750 mmHg which can remain in the syringe for several minutes or indefinitely in some instances.

In another aspect of the disclosure, a structure 142 carrying a filter 144 can be fixedly or detachably connected to body 140 intermediate the cement-carrying sleeve 112 and the negative pressure source 130. In some embodiments, the filter 144 can be a plastic (e.g., high density polyethylene) mesh filter having a mean pore dimension of about 0.1 to 0.5 microns. The filter 144 of some embodiments can have a mean pore dimension of about 0.05 to 10 microns. The filter 144 can be made from many microporous materials, including plastic, metal, and ceramic. Though a filter is shown, the interface can alternatively be a valve, seal, etc. intermediate the polymer powder or bead component and the vacuum source.

The filter 144 can be configured to allow air extraction from the volume of compacted polymer powder 105 in sleeve 112 by initial application of a vacuum from syringe 132. The liquid monomer component 106 when suctioned through the polymer powder 105 in sleeve 112 creates a higher viscosity mixture akin to a wet sand which will not pass through the filter 144. By this means, the filter 144 functions to limit any liquid monomer 106 losses from the saturated mixture, and results in a precise volume of liquid monomer 106 being drawn by vacuum into the sleeve 112 for saturating the polymer powder volume 105.

The filter 144 can advantageously facilitate the operation of the bone cement preparation system 100 according to some embodiments. This is because, the filter 144 can allow sufficient negative pressure to pass through the filter 144 to pull the liquid monomer 106 into the non-liquid 105 component, while also preventing the liquid monomer from simply passing through the sleeve and into the vacuum source. For example, in some embodiments, the filter can clog to prevent flow of the liquid monomer. In some embodiments, the cement mixture can clog the filter to prevent flow of the liquid monomer. In other embodiments, the filter may swell or polymerize once contacted by the liquid monomer to prevent flow through the filter.

If an insufficient amount of liquid monomer 106 is mixed with the non-liquid polymer component 105, the mixture will be starved, i.e. it will have insufficient liquid monomer to begin the curing process in all regions of the mixture. For example, some embodiments of the system advantageously produce a de-aerated, non-clumped and homogeneous bone cement admixture. The exact ratio for the monomer and polymer components can be provided by the packaging of these components, and the system described above can help ensure that substantially none of the liquid monomer escapes the system In some embodiments, the bone cement precursors can be combined to form a self-curing bone cement as a result of a chemical reaction when a polymer component and liquid monomer component interact, along with activators and initiators. For example, some embodiments include the mixing of a PMMA bone cement that can be provided for a treatment, such as, treating a vertebral compression fracture, setting an artificial joint, etc.

In some embodiments, the polymer component 105 is provided in a formulation of bead sizes to cooperate with the monomer volume 106 and negative pressure from the vacuum source to insure that all surfaces of the polymer beads or powder are wetted or saturated. This can be done so that the admixture does not create a polymerizing volume or other volume that clogs the intra-bead spaces to prevent monomer 106 migration from the superior region of the polymer bead volume 105 to the inferior region of the polymer beads.

It can also be important to consider the bead size of the polymer component 105 when determining the pore size of the filter 144. If the bead size is too small compared to the pore size, the initial application of negative pressure to the mixing chamber can clog the filter so that the negative pressure cannot draw the needed liquid monomer into the mixing chamber. This may occur immediately or before sufficient monomer has been drawn into the mixing chamber. If this occurs, it is unlikely that the correct monomer to polymer ratio will be obtained without some further mixing action, such as hand mixing the remaining liquid into the polymer.

The systems and methods described herein can provide many benefits such as not requiring hand mixing. The system can be faster than mixing by hand, and can minimize or eliminate clumping resulting in more uniform cement. For example, in certain embodiments the system can uniformly combine the liquid monomer and the non-liquid polymer in less than about 20 seconds, in about 10 seconds or in only a few seconds. In addition, the system can contain the fumes created by the chemical reaction when the liquid and non-liquid components are combined. For example, the fumes can be contained within the sleeve 112. In some embodiments, at least a portion of the fumes can be drawn into the vacuum source 130.

In addition, the use of negative pressure to draw the liquid into the non-liquid can also provide certain benefits. For example, vacuum can remove the air or gas from the non-liquid. This space can be filled with the liquid to get a more even and uniform saturation. Were the liquid to be forced into the non-liquid, such as by injecting the liquid, the air is not necessarily removed. Injection can also, in some instances, result in air pockets, clumps, and other areas of non-uniformity. Hand mixing can result in similar problems. In some embodiments, the use of vacuum can substantially, if not completely, remove these problems.

Returning now to FIG. 1, as can be seen, in some embodiments a pressure relief valve 145 is provided which can be used to limit the amount of negative pressure in the syringe 132.

In one embodiment, the body 140 carries a valve indicated at 148 for closing the channel 136 that runs through the body 140. The valve 148 can be used as follows. After closing the valve 148, the lockable plunger assembly 134 is retracted proximally in chamber 135 (as indicated by the arrow in FIG. 1) and locked in this retracted position. With the valve 148 closed, this action provides a selected negative pressure or vacuum inside the chamber 135. Thereafter, with the sleeve 112 held in a vertical position, a liquid monomer 106 can be poured into a funnel 150 and then the valve 148 can be moved to an open position to create suction to move the monomer 106 into and through polymer powder 105 in the sleeve 112. In this way, the polymer powder 105 can be thoroughly and controllably saturated with the monomer 106 to initiate the polymerization of the bone cement 110.

The system of FIG. 1 further can include a funnel mechanism 150 for assisting the step of pouring the requisite volume of liquid monomer 106 into the open end 117 of the proximal end 116 of the sleeve 112. As depicted in FIG. 1, the funnel mechanism 150 can be a funnel member attachable to sleeve 112. The volume of the funnel can be sized to contain a volume of monomer 106 required to saturate the volume of polymer powder 105 in sleeve 112. The funnel member 150 can be fabricated of a clear plastic or other material and can have a fluid-tight fitting, such as an o-ring, to couple to sleeve 112.

In one embodiment, the funnel mechanism 150 or the proximal end of sleeve 112 can carry a filter, seal or valve 155. The filter, seal or valve 155 can be used for maintaining the polymer powder 105 in the sleeve before use. In some embodiments the filter 155 is a course filter configured for maintaining the polymer powder 105 in the sleeve 112 while minimizing resistance to flow of liquid monomer 106 through the filter 155. In one example, the funnel member 150 and filter 155 are detachably coupled to the proximal end 116 of sleeve 112 after the polymer powder 105 is packed into the sleeve 112. In another example, a detachable filter 155 can be coupled to the sleeve 112 after the polymer powder 105 is placed in the sleeve 112. In one embodiment, the filter can be a high density polyethylene with a mean pore dimension of about 25 microns.

In some embodiments, a system 100 for preparing a curable bone cement 110 can include an elongated sleeve 112 having an elongated interior space 114 carrying less than 5 cc of a non-liquid polymer component 105 of a curable bone cement, and a negative pressure source 130 configured for detachable communication with the interior space for vacuum infusion of a liquid monomer component 106 into the non-liquid polymer component 105. A system for preparing bone cement, according to some embodiments, can include a non-liquid polymer component of a curable bone cement disposed within an interior space of a plurality of sleeve members 112, and a negative pressure source configured for detachable communication with the interior spaces for vacuum infusion of a liquid monomer component into the non-liquid polymer component. The various systems for preparing bone can further include a cement ejection mechanism coupleable to the sleeve for ejecting the bone cement from the sleeve into bone, the ejection mechanism selected from the group of, or a combination of: manually actuated piston-like member, hydraulically actuated piston, pneumatically actuated piston; a cable-driven piston, and a computer-controlled driver of a piston.

Systems for preparing bone cement, including those described above, can include a filter 144 intermediate the sleeve 112 and the negative pressure source 130. In one embodiment, the system can use a swellable porous membrane intermediate the sleeve 112 and the negative pressure source 130 for preventing any monomer losses from flowing through the membrane. The system can have a filter, seal and/or cap member at one or both ends of the sleeve for maintaining compacted polymer powder 105 in the sleeve member 112 for shipping and storage. In some embodiments, the sleeve 112 can be shipped with the funnel 150 and filter 155 containing the polymer powder 105 at one end and the body 142 and filter 144 capping the other end. In other embodiments, the body 140 can be attached to the sleeve for shipping.

Figure 2:
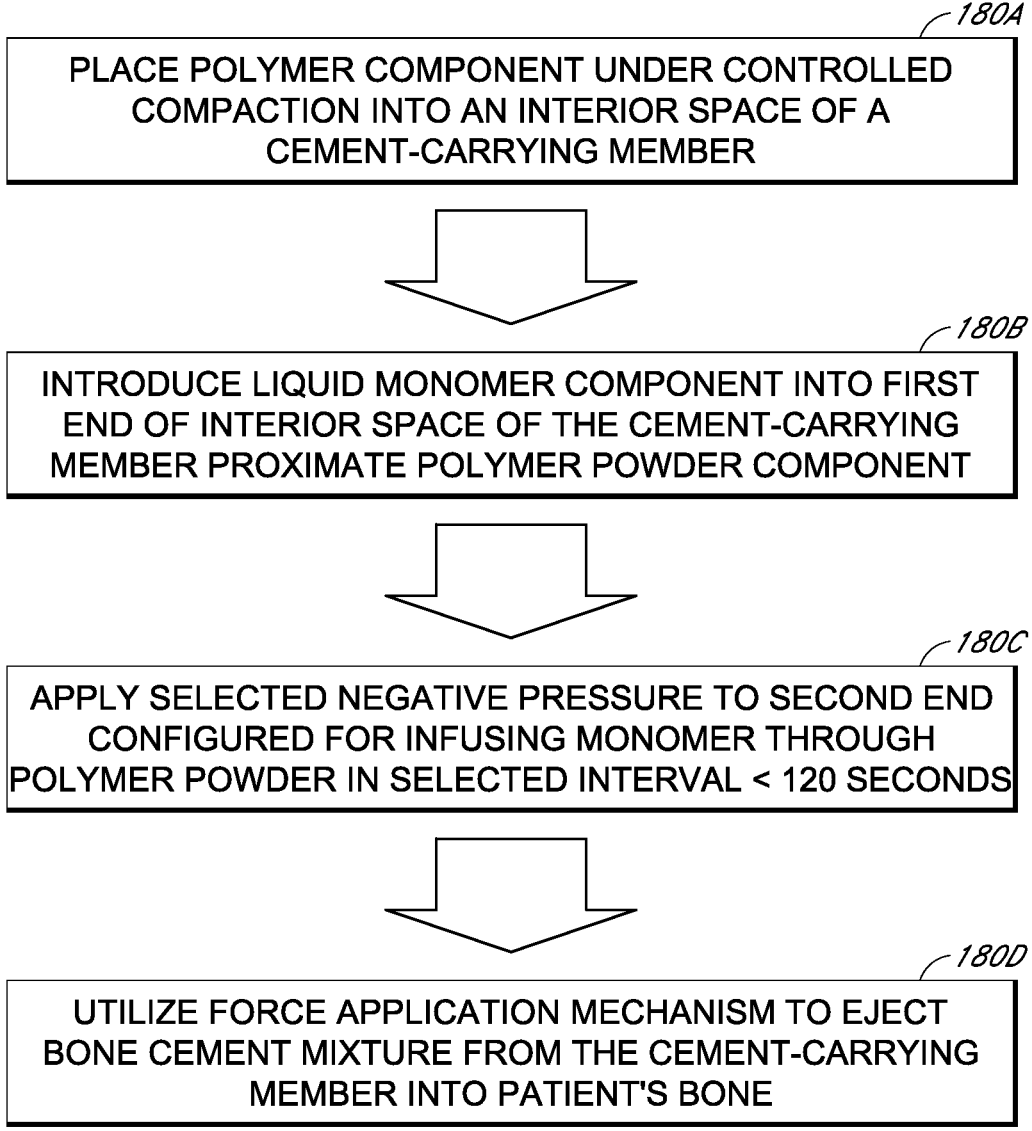
FIG. 2 is a block diagram of a method for utilizing the system of FIG. 1.

In one method illustrated in FIG. 2, the steps of controllably saturating the polymer powder with monomer can include: (i) placing a polymer powder component under controlled compaction into an interior space of a cement-carrying member indicated at 180A; (ii) introducing the liquid monomer component into a first end of the interior space of cement-carrying member proximate the polymer powder component indicated at 180B; (iii) applying a selected negative pressure to the opposing end of the interior space with the negative pressure configured for infusing monomer through the polymer powder in a selected time interval of less than 120 seconds, less that 90 seconds, less than 60 seconds, less than 45 seconds or less than 30 seconds, as indicated at 180C; and (iv) utilizing a force application mechanism to eject the saturated bone cement mixture from the cement-carrying member into a patient's bone, indicated at 180D.

Figure 3:
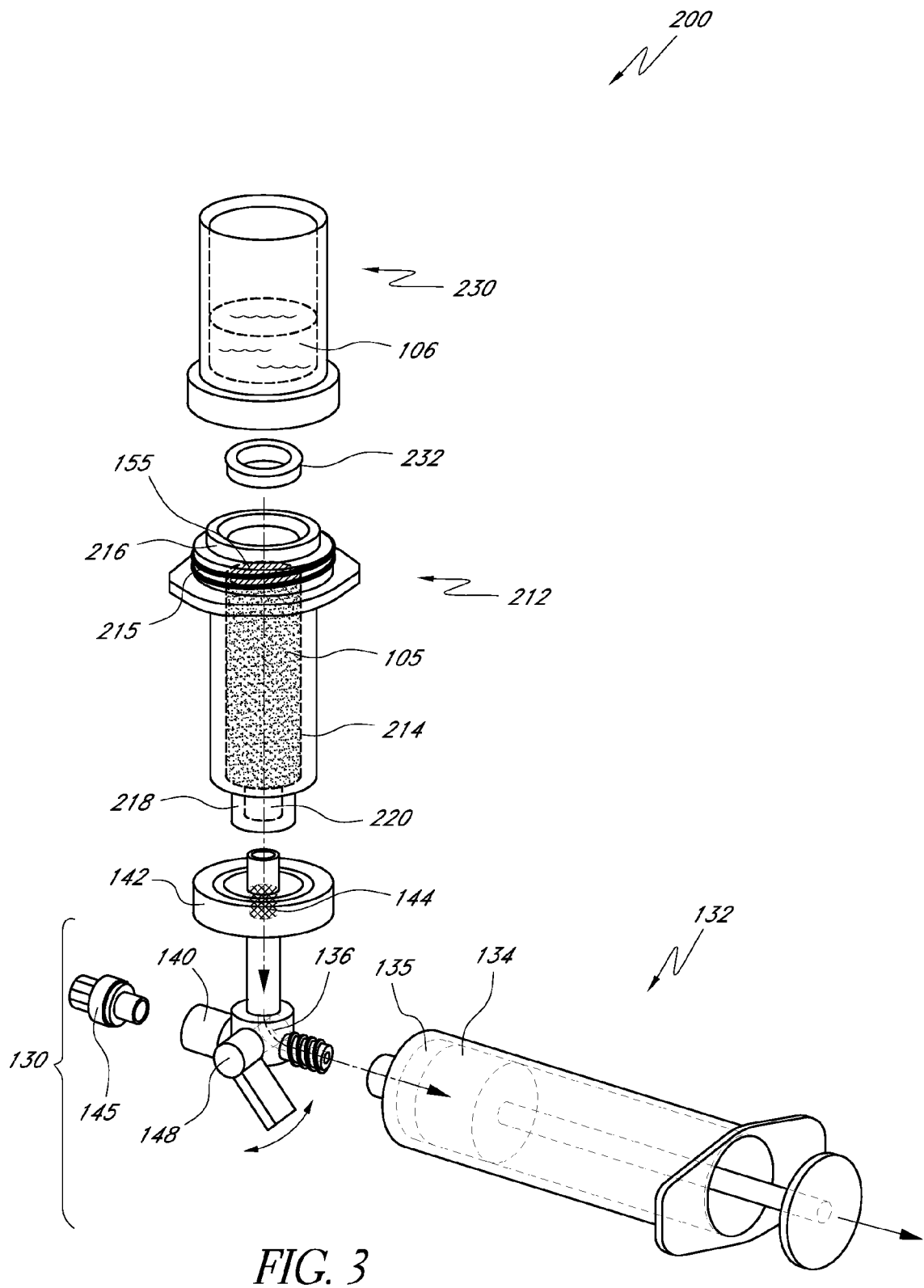
FIG. 3 is another bone cement preparation system similar to that of FIG. 1.

FIG. 3 illustrates another system 200 for combining a liquid monomer component 106 and a polymer powder component 105. In this system 200, the negative pressure source 130 is similar to that described above. The cement-carrying member 212 of FIG. 3 can have a syringe body configured for coupling to any manually actuated or hydraulically actuated plunger (not shown) for advancing in chamber 214. In one embodiment, the cement-carrying member 212 has a fitting 215 at its proximal end 216 for coupling to a hydraulic drive mechanism as illustrated in U.S. patent application Ser. Nos. 11/469,769 filed Sep. 1, 2006; Ser. No. 12/024,969 filed Feb. 1, 2008; Ser. No. 12/112,477 filed Apr. 30, 2008; 61/067,479, filed on Feb. 28, 2008; 61/067,480, filed on Feb. 28, 2008; 61/124,336, filed on Apr. 16, 2008; 61/190,375 filed Aug. 28, 2008; and 61/124,338 filed Apr. 16, 2008, all of which are incorporated by reference herein in their entirety.

The distal end 218 of member 212 can include a fitting 220 (such as a Luer fitting) for coupling member 212 to structure 142. Structure 142 can carry a filter 144 as described above and can be fixedly or detachably connected to body 140. In FIG. 3, the funnel member 230 can be detachably coupled to fitting 215 and a seal or an o-ring 232 can be adapted for making a liquid tight fit. A filter 155 also can be provided to maintain the polymer powder in the member 212 as described previously.

In order for a predetermined negative pressure to cause monomer 106 to optimally saturate the polymer powder 105 within the time intervals described above, it has been found that several elements can require careful control, including (i) the shape and mean dimensions of the constituent polymer powder(s); (ii) the compaction of the polymer powder in the interior chamber of the sleeve; (iii) the initiators within the polymer powder; (iv) the height, cross-section, and volume of the column of polymer powder; and (v) the level of vacuum applied and whether the vacuum level is provided at a constant rate over the saturation interval or whether the vacuum is provided from an evacuated chamber such that the applied negative pressure varies over the saturation interval. Some parameters of the polymer powder 105 are described further below.

In one embodiment, a method of providing an optimized saturation interval can use an initial pressure developed by an evacuated chamber (e.g., such as a syringe as in FIGS. 1 and 3) of at least 200 mmHg vacuum, at least 250 mmHg vacuum, or at least 350 mmHg vacuum. In the embodiment depicted in FIG. 3, the interior chamber 214 has a diameter of about 16 mm and length of about 60 mm thus providing a volume of approximately 12 cc. With a vacuum of about 400 mmHg, the monomer 106 will controllably saturate the polymer powder 105 in about 60 seconds. This is using a polymer powder formulation comprising first and second volumes of intermixed polymer particles wherein the first volume of PMMA particles has greater than about 0.5 wt. % benzoyl peroxide (BPO) and the second volume of PMMA particles comprises less than about 0.5 wt. % BPO, on the basis of the total weight of the polymer powder component. Further, the first volume of PMMA particles has a mean diameter less than about 50 μm and the second volume of PMMA particles has a mean diameter greater than about 100 μm. Other polymer powder and monomer formulations can be used and some formulations suitable for the system are found in U.S. patent application Ser. No. 12/395,532 filed Feb. 27, 2009 and Ser. No. 12/578,163 filed Oct. 13, 2009 and incorporated herein by reference in their entirety and made a part of this specification.

Another method is shown in the block diagram of FIG. 4. Steps of controllably saturating a polymer powder with a liquid monomer can include: (i) placing a polymer powder component under controlled compaction into an interior space of a cement-carrying member indicated at 150A of FIG. 4; (ii) introducing the liquid monomer component into a first end of the interior space of cement-carrying member proximate the polymer powder component as indicated at 150B; (iii) applying a selected negative pressure to the opposing end of the interior space with the negative pressure as indicated at 150C; (iv) controlling the volume of liquid monomer interacting with the polymer with a controlled porosity filter indicated at 150D; and (v) utilizing a force application mechanism to eject the saturated bone cement mixture from the cement-carrying member into a patient's bone, indicated at 150E in FIG. 4.

In one embodiment, a system for preparing bone cement, includes a plurality of elongated sleeves having first and second ends; a powder component of a curable bone cement disposed within interiors of the sleeves; and a negative pressure source configured for detachable coupling to an end of each sleeve for vacuum infusion of a liquid monomer component into the powder component. The system can further include a computer controller for controlling a negative pressure level applied to each sleeve and/or for selective application of negative pressure level to a particular sleeve over a time interval. In another embodiment, a system for preparing bone cement can have an elongated sleeve having first and second ends, a powder component of a curable bone cement disposed within an interior of the sleeve, and a filter detachably coupled to an end of the sleeve. The system may further include a negative pressure source configured for detachable coupling to the filter for vacuum infusion of a liquid monomer component into the powder component.

Figure 5:
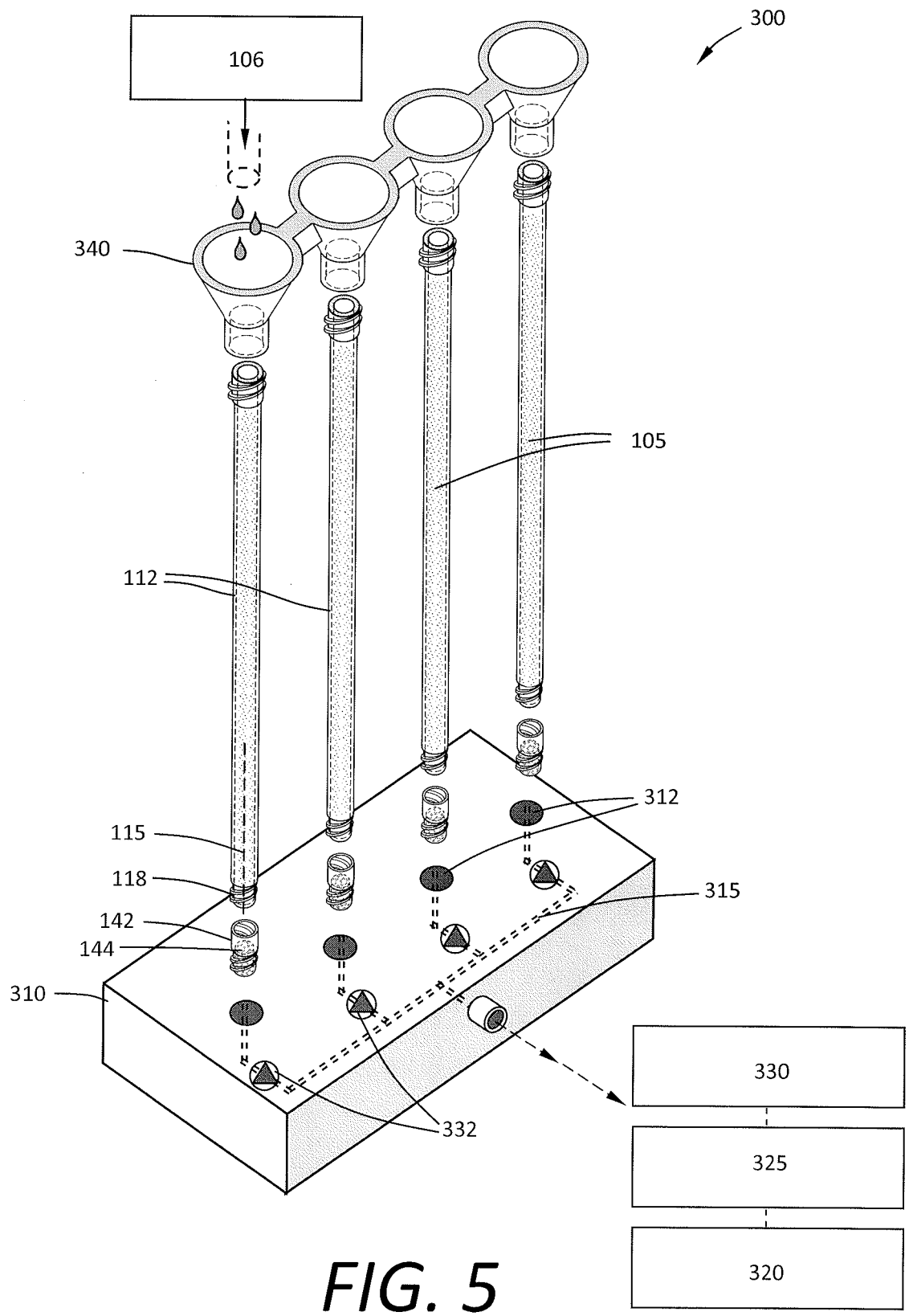
FIG. 5 is a perspective view of another system for bone cement preparation by vacuum saturation mixing in a plurality of sleeves.

FIG. 5 illustrates another system 300 for preparing a bone cement for a vertebroplasty, osteoplasty, or other procedure which system utilizes a plurality of cement-carrying sleeves 112. The sleeves 112 can each carry various amounts of polymer powder, such as less than about 5 cc, or less than about 2 cc. As shown, a base or stand structure 310 is provided that has receiving ports 312 for receiving distal ends 118 of a plurality of sleeves 112 or the detachable filter assemblies 142 similar to that of FIG. 1. The base 310 can be configured to receive from 2 to 10 or more sleeves 112, and the ports 312 can communicate though channels 315 with a negative pressure source 320. The negative pressure source 320 can be, for example, a syringe mechanism as in FIG. 1 or a vacuum pump such as a hospital vacuum line. A pressure regulator 325 and controller 330 can also be provided, as well as, manual or computer-controlled valves 332 to close off selected portions of channels 315. The pressure regulator 325 can regulate and control the vacuum pressure from the negative pressure source 320 to the base structure 310 and/or the sleeves 112.

The system 300 and controller 330 can be used or programmed to infuse the monomer 106 into the polymer powder 105 in the sleeves 112. The system and controller can also be used to prepare the sleeves 112 with volumes of cement at the same time or at selected time intervals. The controller 330 can have a signal system such as aural or visual signals to indicate when to use a particular sleeve 112, to add monomer to a sleeve 112 or the like. In one embodiment, the system 300 includes a funnel assembly 340. As in FIG. 5, the funnel assembly 340 can be a unitary system that can be used when pouring monomer into one or more of the sleeves 112. The funnel assembly 340 can connect to the sleeve(s) 112 with a slip-fit, friction fit, snap fit, locking fit, etc. The system 300 can allow the physician to control the time at which different sleeves 112 have a cement volume available at a selected polymerization endpoint, and can further allow for controlling the batch size of cement selected for saturation mixing.

Figure 6A:
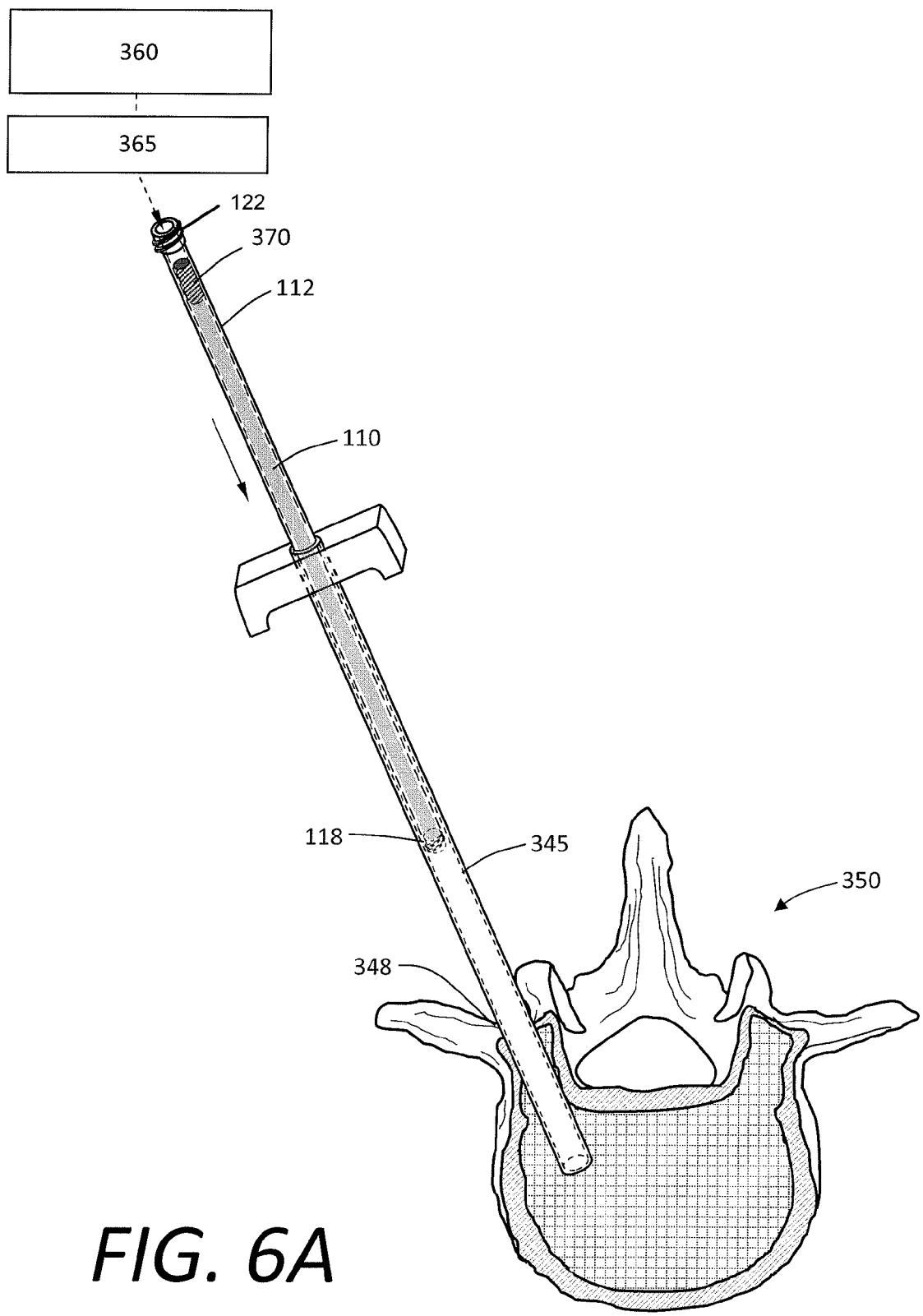
FIG. 6A is a graphical representation of a step involved in certain methods.
Figure 6B:
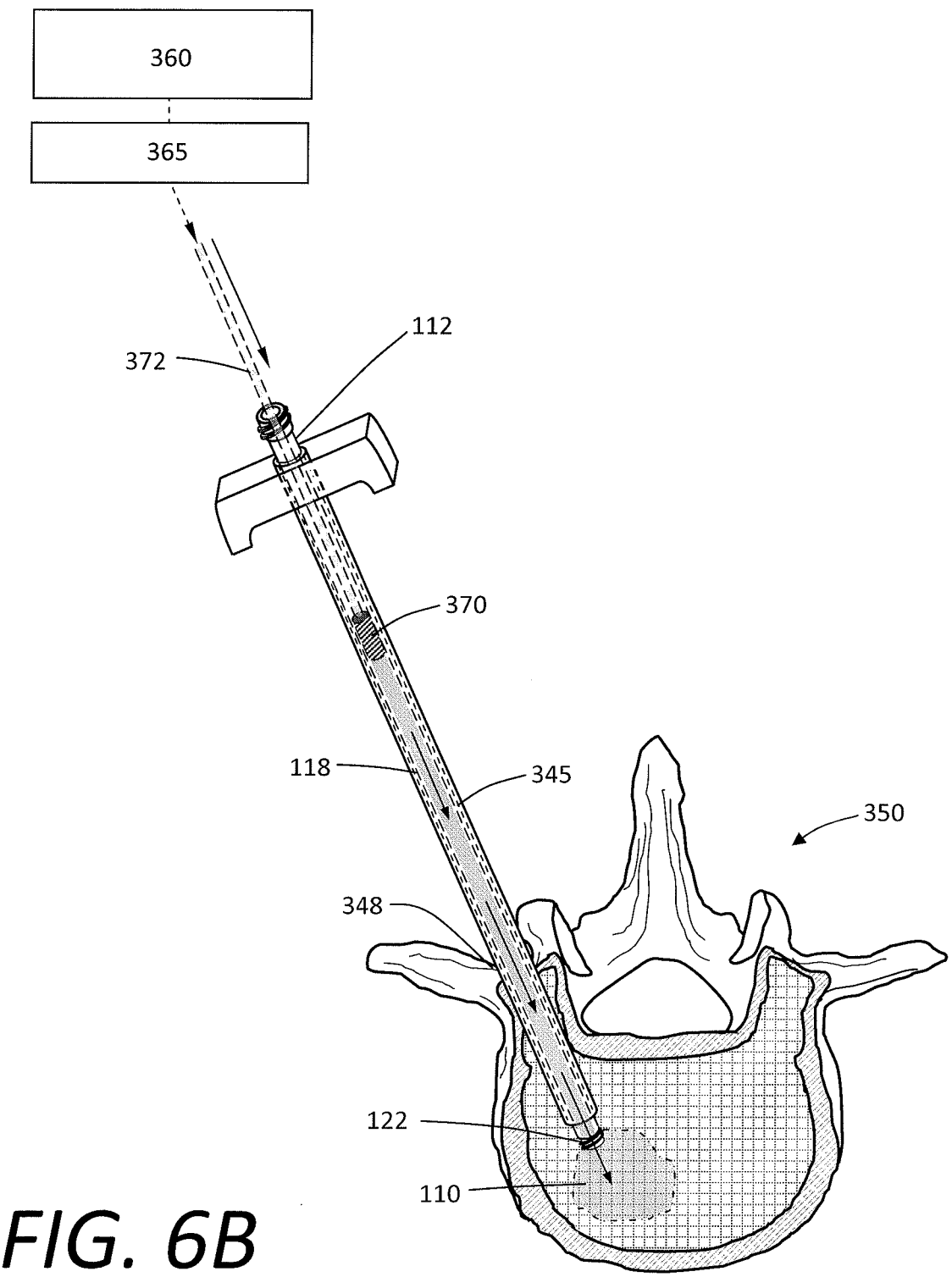
FIG. 6B is a subsequent step of injecting cement into a vertebra.

In a method of using the system 300 of FIG. 5, the individual sleeves 112 can have monomer 106 saturated into the polymer powder 105 followed by a post-saturation interval of 1 to 3 minutes or more to allow the cement mixture 110 in the sleeve to reach a desired viscosity. Thereafter, in one method as shown in FIG. 6A, a sleeve 112 is inserted into a cannula 345 previously inserted through a pedicle 348 in vertebra 350. A pressure mechanism 360, such as a hydraulic source, and a controller 365 are then coupled to the sleeve 112. This can be by way of a proximal fitting 122 or other type of connection. FIG. 6B shows how a piston 370 disposed in the sleeve 112 can be moved distally by a shaft 372 or fluid (liquid or gel) flow to thus eject cement mixture 110 into the interior of the vertebra 350.

In a method corresponding to the block diagram shown in FIG. 7, the steps of controllably saturating the polymer powder and using the cement mixture can include: (i) placing a PMMA polymer powder component of a curable bone cement under controlled compaction in interior spaces of about less than or equal to 5 cc of a plurality of cement-carrying members as indicated at 380A of FIG. 7; (ii) introducing the liquid monomer component into a first end of the interior spaces of the cement-carrying members as indicated at 380B; (iii) utilizing a computer-controlled application of negative pressure to the opposing end of the interior space to infuse monomer through the polymer powder as indicated at 380C; and (iv) utilizing a force application mechanism to eject the bone cement mixture from the cement-carrying member into a patient's bone, as indicated at 380D.

Figure 8:
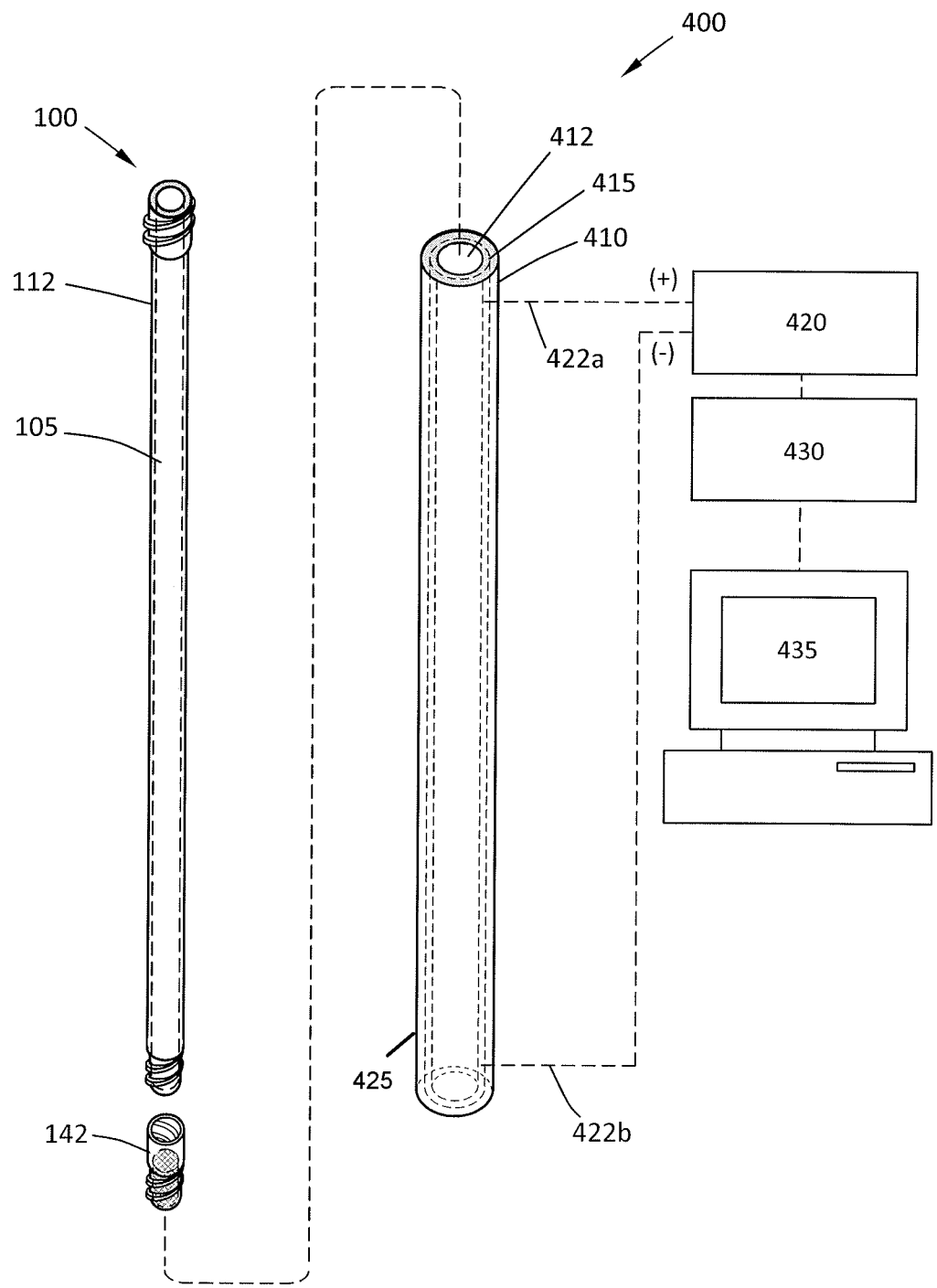
FIG. 8 is a perspective view of another system for bone cement preparation by vacuum saturation mixing and pre-heating of the polymer powder in a sleeve.

FIG. 8 illustrates a heat applicator system 400 configured for use in conjunction with the systems 100 and/or 300 of FIGS. 1 and 5. The system 400 can be adapted for controlled acceleration of the polymerization of a monomer-saturated polymer powder in one or more elongated cement-carrying sleeves 112 that each have a small cross-section as described above. In FIG. 8, the cement-carrying sleeve 112 and detachable filter-carrying member 142 can be the same as described previously. A funnel member 150 and proximal filter 155 (not shown) can also be used.

A heater applicator system 400 can include an elongated member 410 with a receiving bore 412 therein dimensioned to receive substantially the length of the sleeve 112. As depicted in FIG. 8, the heat applicator utilizes a heating element or emitter 415, such as a resistive heating element, with bore 412 therein for conducting heat to the sleeve 112 to thereby heat the polymer powder, but the system can include any heat emitter mechanism within or about an elongate receiving bore 412 that is dimensioned to receive sleeve or sleeves 112. In the embodiment of FIG. 8, an outer concentric portion 425 of the member 410 can have an insulator layer of any thickness necessary to provide thermal insulation, and can include voids, air gaps, spaces with a partial vacuum, spaces with aerogel insulators, spaces with combination vacuum and aerogels and the like to allow for handling of the member 410 and/or added safety when in use. FIG. 8 also shows a heating element 415 that is a PTCR (positive temperature coefficient of resistance) material as is known in the art of constant temperature heaters. Opposing ends of sides of the heating element 415 are coupled to opposing polarity leads 422a and 422b of an electrical source 420, and computer controller 430 that can include a display 435. While the PTCR resistive heater is described above, a system and method can utilize at least one of inductive heating, resistive heating, light energy heating, heated air or gas circulation, RF heating, microwave heating, magnetic heating, and heated liquid circulation. The heating system can be configured to convectively heat, for example, a bone cement component, a member that contains a bone cement component, or a structure or space that is adjacent a member that contains a bone cement component.

Figure 9:
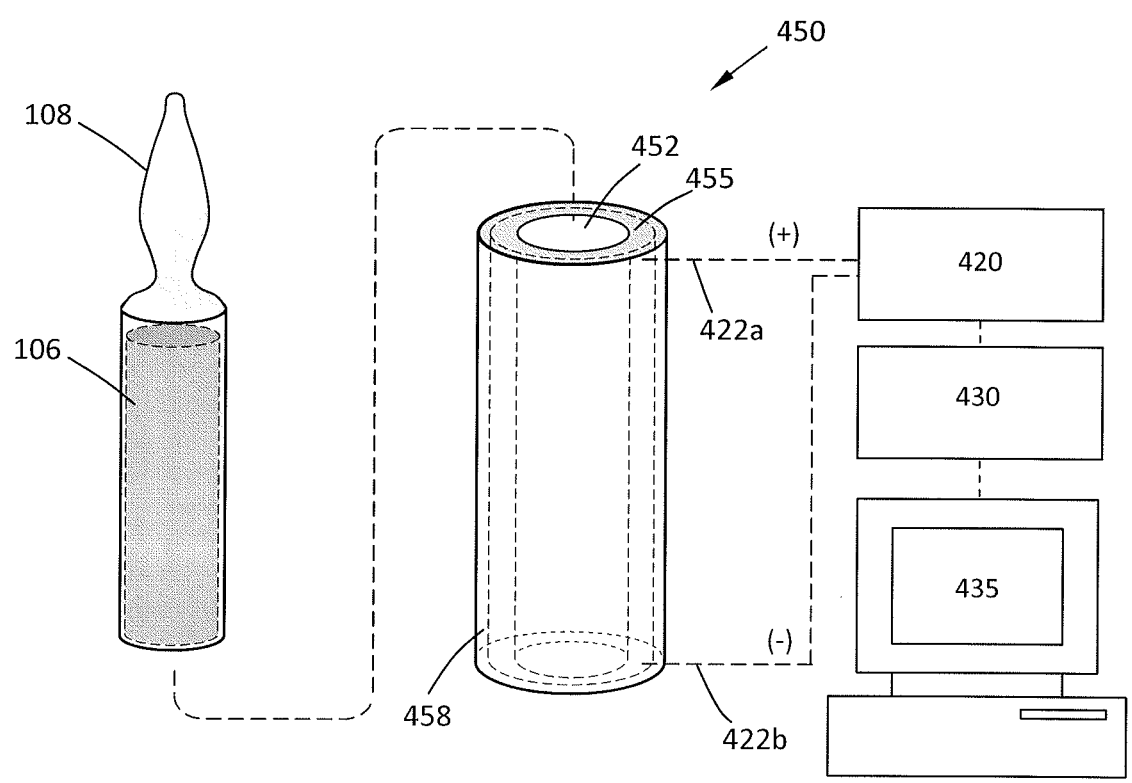
FIG. 9 is a perspective view of another system for pre-heating of a liquid monomer.

FIG. 9 illustrates another system that can include a heat applicator system 450 functionally equivalent to that of FIG. 8 except configured for heating the monomer component 106 in vial 108 for use in conjunction with heated polymer powder 105 as described above. In some embodiments, either or both of the systems of FIGS. 8 and 9 can be used. As depicted in FIG. 9, a member 450 with bore 452 therein utilizes a PTCR resistive heating element or emitter 455 for conducting heat to a standard vial 108 to thereby heat the liquid monomer 106. Also in FIG. 9, an outer concentric portion 458 has an insulator layer as described above. Again, the scope can include any heat emitter mechanism suitable for heating the monomer, and FIG. 9 depicts heating element 455 again coupled to opposing polarity leads 422a and 422b of electrical source 420 together with controller 430 and display 435.

In a method of using the system of FIG. 8 and optionally the system of FIG. 9, the steps can include (i) providing liquid and non-liquid cement components of a curable bone cement that post-mixing or post-saturation is characterized by a pre-determined first time-viscosity curve at an ambient temperature, (ii) heating at least one of the cement components prior to mixing or saturation to at least about: 30° C., 32° C., 34° C., 36° C., 38° C., 40° C., 42° C., 44° C., 46° C., 48° C. or 50° C., and (iii) mixing the cement components wherein the at least one heated cement component provides a cement mixture characterized by an altered second time-viscosity curve. The system can heat the polymer powder 105 in sleeve 112 and/or the monomer 106 in vial 108 to the desired temperature(s) within one to five minutes, and a display can indicate the temperature or a time to initiate monomer-polymer saturation with the systems described above.

Figure 10:
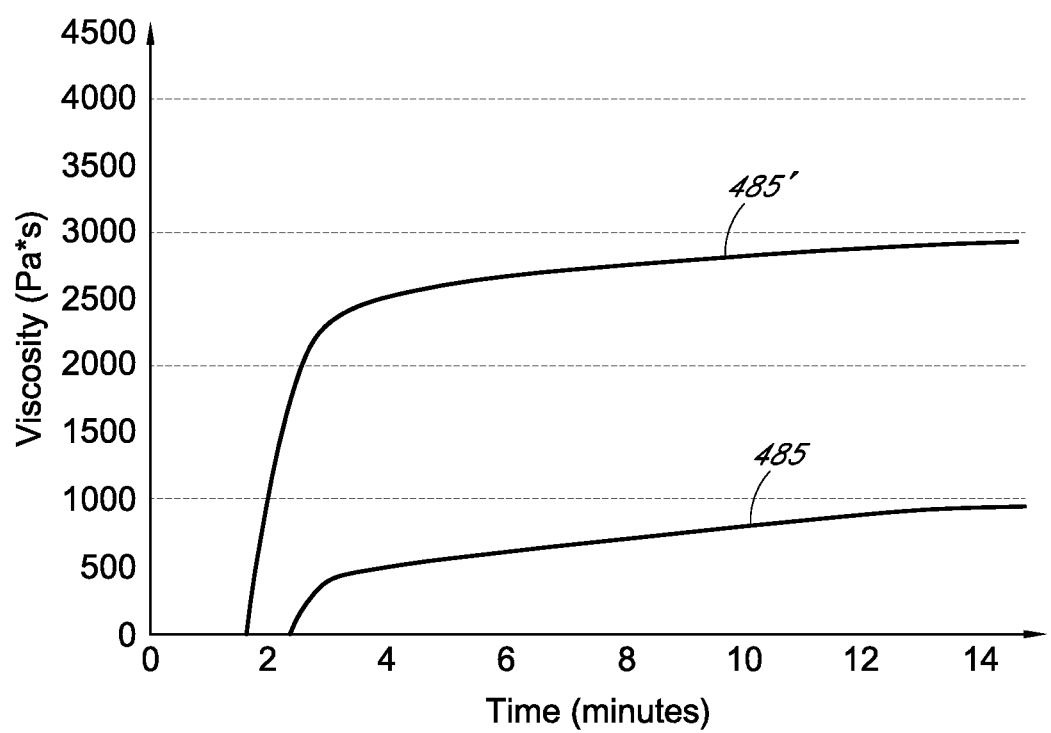
FIG. 10 is a representative time-viscosity curve of a curable bone cement with and without using a pre-heating system.

In another aspect of a method, the pre-heating of the polymer powder and/or the monomer can provide an altered or second time-viscosity curve that is characterized by the mixture reaching a viscosity of at least 1000 Pa·s in less than 2 minutes post-mixing, or by the mixture reaching a viscosity of at least 1500 Pa·s in less than 3 minutes as depicted in FIG. 10. In FIG. 10, a first time-viscosity curve 485 is shown for a cement mixture that is saturated or mixed at about 20° C. ambient temperature. FIG. 10 shows an altered or second time-viscosity curve 485' for the same cement mixture when the polymer powder is pre-heated to have a uniform temperature of about 40° C. prior to saturation with monomer. The time-viscosity curves 485 and 485' are approximated from a polymer powder 105 heated to 40° C., with the polymer powder and monomer formulations found in U.S. patent application Ser. No. 12/395,532 filed Feb. 27, 2009.

Another method of preparing a cement can include the steps of (a) providing a first liquid component and a second non-liquid component of a curable bone cement; (b) placing the cement components, prior to mixing, in a system that controls the temperature of the first and second components within a range of 2° C. or 1° C. on either side of a predetermined temperature; and (c) exposing the non-liquid component to the liquid component while maintaining particles of the non-liquid component in a fixed relationship within a container. It has been found that widely varying ambient temperatures in operating rooms, and cement component storage rooms in hospitals, contribute to high variability in time-viscosity curves of mixed cements. The heating systems described herein can be used to help ensure that cement precursors are at a pre-selected temperature just prior to saturation mixing, such as within a small range of variability, for example 2° C. or 1° C.

A method is shown in the block diagram of FIG. 11, wherein the steps of controllably saturating the polymer powder can include: (i) placing a polymer powder component of a curable bone cement under controlled compaction in interior spaces of a plurality of cement-carrying members as indicated at 480A of FIG. 11; (ii) pre-heating the powder component to a pre-determined temperature in the range of 30° C. to 60° C. and/or pre-heating the monomer to a similar temperature; (iii) mixing a monomer component with the polymer component; and; (iv) utilizing a force application mechanism to eject the bone cement mixture from the cement-carrying member into a patient's bone, as indicated at 480D of FIG. 11.

Figure 12:
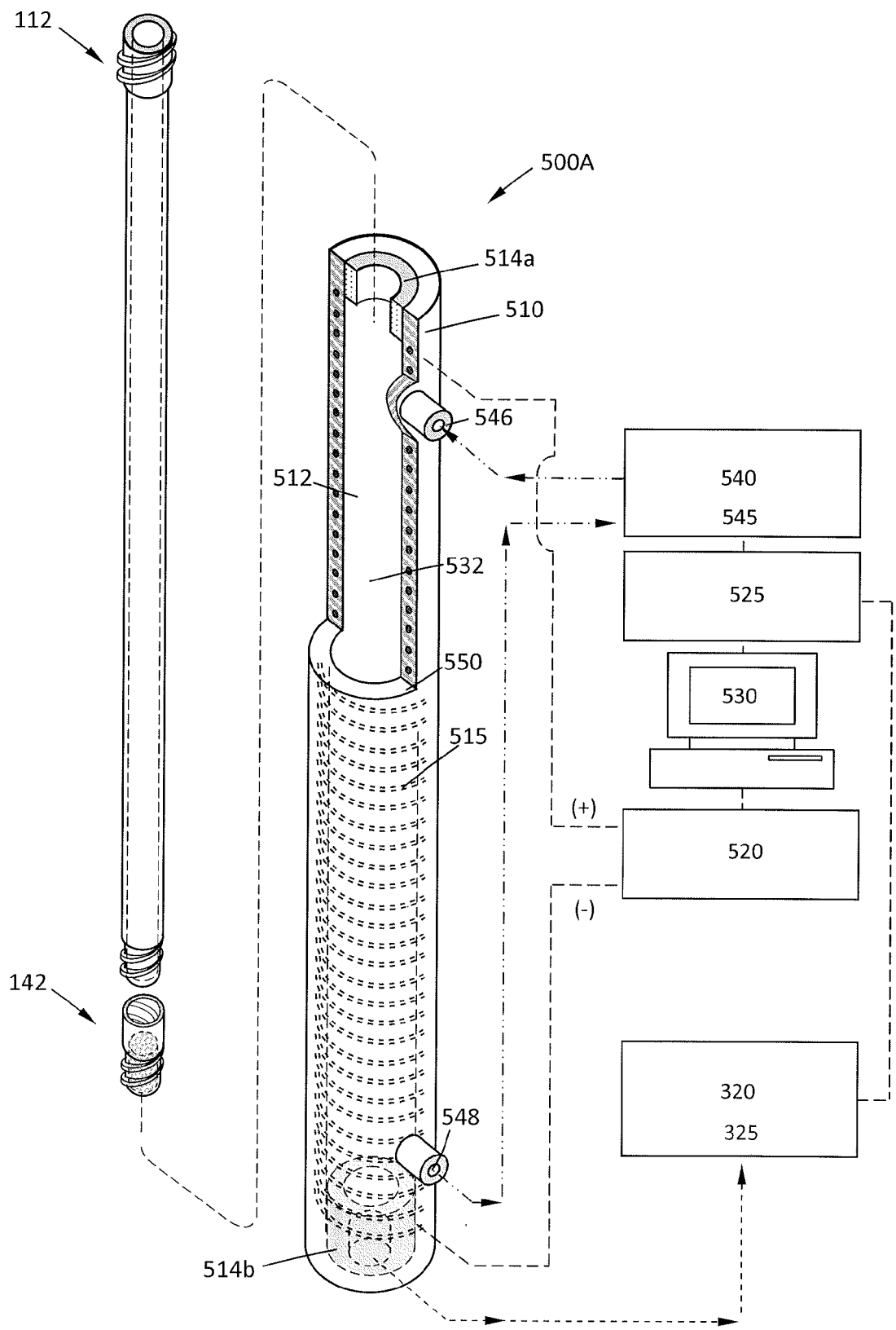
FIG. 12 is a perspective view of another system for bone cement preparation by vacuum saturation mixing, pre-heating of the polymer powder, and cooling the cement mixture post-mixing.

FIG. 12 illustrates an embodiment of a system 500A for preparing a curable bone cement within sleeve 112 as described above and having a receiving structure 510 for receiving sleeve 112. Receiving structure 510 can include both a heating mechanism and a cooling mechanism that are computer controlled. This can allow for complete temperature management of the bone cement prior to mixing and post-mixing thus allowing the physician to have a pre-determined cement viscosity and also to provide a very long time interval during which one or more cement-carrying sleeves 112 may be utilized.

The system of FIG. 12 illustrates elongated member 510 with a receiving bore 512 therein that is dimensioned to receive substantially the length of the sleeve 112. Resilient seals or collars 514a and 514b are dimensioned to fit closely around the exterior of sleeve 112. In one embodiment depicted in FIG. 12, the heat applicator utilizes an inductive coil 515 around bore 512 that is coupled to RF source 520, computer controller 525 and display 530. The coil 515 can be actuated to inductively heat the sleeve 112, where the sleeve 112 is fabricated of a material that can be inductively heated, such as a biocompatible stainless steel (e.g., SS316). It should be appreciated that a PTCR resistive heater as described above can be used, as can other heating devices and methods, such as resistive heating, light energy heating, heated air or gas circulation, microwave heating, magnetic heating, or heated liquid circulation.

In some embodiments, the sleeve 112 is heated with light energy (e.g. LEDs) or an inductive coil 515. In addition, a free space 532 around the sleeve 112 in bore 512 can be used with a cooling mechanism, such as to receive flow of a cooling fluid from a cooling fluid source 540. In one embodiment, the cooling fluid can be a cooling gas from source 540 and pressure regulator 545, such as a liquid $CO_2$, liquid nitrogen or the like.

In FIG. 12, the cooling fluid can flow into inflow port 546 communicating with space 532 and then out outflow port 548. An outer concentric portion 550 of structure 510 can also use an insulator layer as described above.

A heating system can be used to pre-heat the cement precursors as described above. The system can also include a negative pressure source 320 and a regulator 325 coupleable to the sleeve 112 and filter structure 142 as described previously to saturate the polymer powder in sleeve 112 with the monomer. Post-saturation, the system and controller can be programmed to maintain a selected temperature in the cement-carrying sleeve 112. For a selected cooled temperature, the system and controller can modulate the flow of a cooling gas or fluid until the sleeve 112 is needed for use. At that time, the heating system can optionally be used to heat the cement in sleeve 112 to ambient room temperature or another selected temperature for injection into bone.

In general, the bone cement and system of FIG. 12 can include: (i) a liquid monomer component 106 and a non-liquid polymer component 105 of a curable bone cement, the polymer component carried in interior space(s) of one or a plurality of elongated cement-carrying members, (ii) a structure for receiving one or a plurality of the cement-carrying members; (iii) a heating assembly on the structure for applying heat to the interior space(s) of one or the plurality of elongated cement-carrying members, and (iv) a cooling assembly on the structure for subtracting heat from the interior space(s) of one or the plurality of elongated cement-carrying members.

The block diagram of FIG. 13 describes a method wherein the steps of preparing and using a bone cement can include: (i) placing a polymer powder component of a curable bone cement under controlled compaction in the interior space of at least one cement-carrying member as indicated at 580A of FIG. 11; (ii) pre-heating the powder component to a predetermined temperature in the range of 30° C. to 60° C. and/or pre-heating the monomer to a similar temperature; (iii) mixing a monomer component with the polymer component; (iv) utilizing a computer-controlled cooling system to cool the bone cement in the cement-carrying member(s) as indicated at 580D of FIG. 13; and (v) utilizing a force application mechanism to eject the bone cement mixture from cement-carrying member(s) into a patient's bone, as indicated at 580E of FIG. 13. The method can also include the step of heating the cement after the cooling step, but before injection into bone to accelerate the polymerization of the cement mixture.

Figure 14:
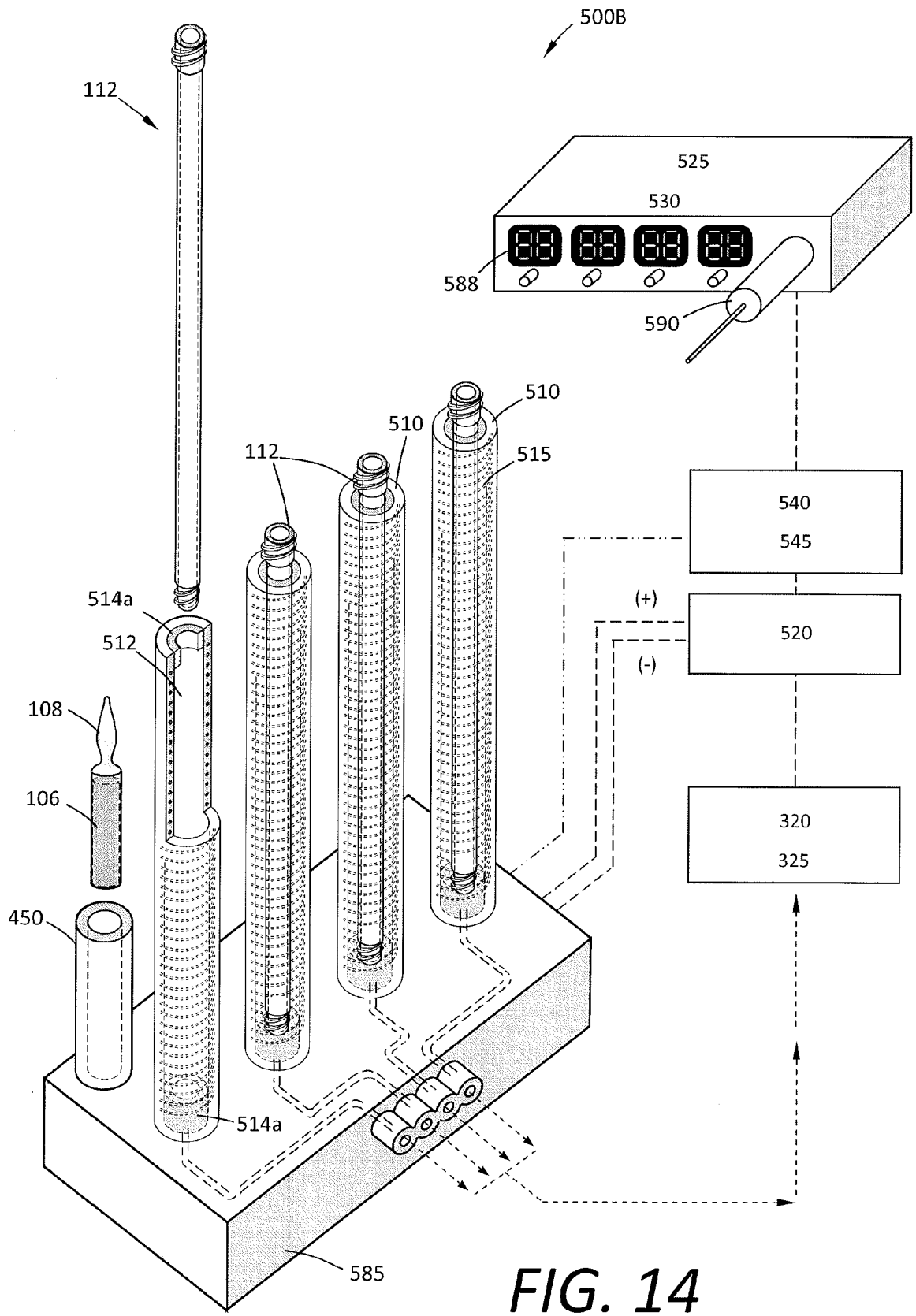
FIG. 14 is another embodiment of a cement injector system with integrated components.

FIG. 14 illustrates an integrated system 500B that includes a base or stand assembly 585 with a plurality of structures 510 and heaters 515, such as inductive heaters similar to that of FIG. 12, that can receive a plurality of cement-carrying members 112. The plurality of structures 510 can range from 2 to 10 or more. The system 500B further includes a heating source 520, a computer controller 525, a display 530, negative pressure source 320 and regulator 325, a cooling gas source 540 and a pressure regulator 545 similar to that shown in the embodiment of FIG. 12. The system can include a heating assembly 450 for pre-heating monomer 106 in vial 108 as shown in FIG. 9. In some embodiments, the heating source 520 can be an RF heating source.

In use, it can be understood that the physician can select any number of cement-carrying structures 112 for a procedure, and then pre-heat and mix the cement, and then controllably cool the cement until needed in the course of a procedure. The system is particularly useful in that all cement can be mixed in advance, and independent of how many delays in the procedure or the length of the procedure, bone cement of a known, controlled viscosity can always be readily available.

In one embodiment as in FIG. 14, the display 530 can include indicators 588 of the temperature of each cement-carrying sleeve 112, and the controller can also include a hydraulic drive mechanism 590 as described in U.S. patent application Ser. No. 12/345,937 filed Dec. 30, 2008.

A system for preparing bone cement similar to FIG. 14 can include: (i) a liquid monomer component and a non-liquid polymer component of a curable bone cement, the polymer component carried in interior spaces of a plurality of elongated cement-carrying members; (ii) a structure for receiving a plurality of the members; (iii) a negative pressure source configured for detachable communication with the structure and the interior spaces of the plurality, of the members; and (iv) thermal management comprising computer controllable heating and cooling systems for controlling the temperature and viscosity of the bone cement prior to injection into bone.

Figure 15:
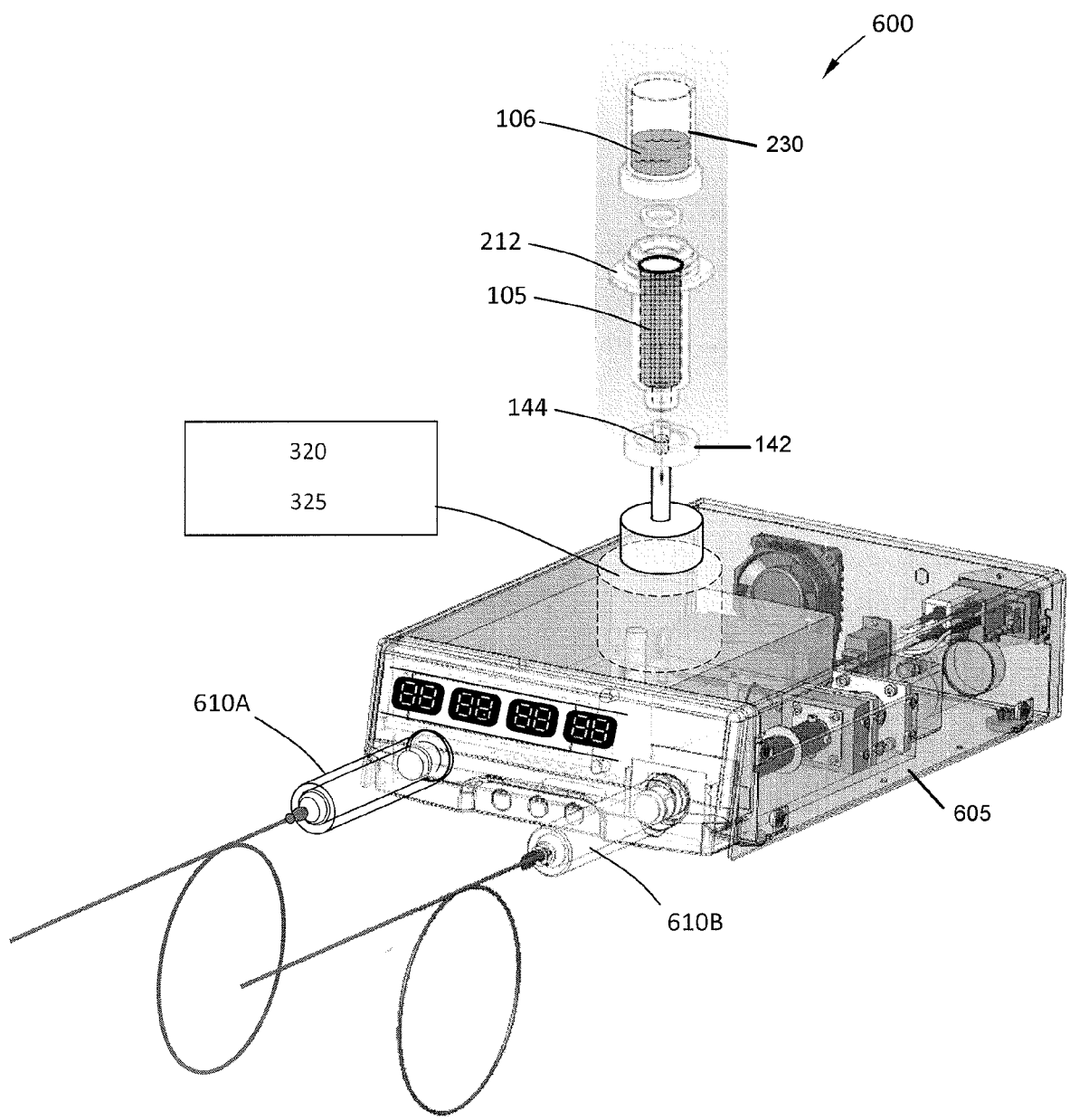
FIG. 15 is an embodiment of a cement injector system with first and second hydraulic assemblies and built-in vacuum saturation components.

FIG. 15 illustrates a system 600 for use with a bone cement injector system, similar to those described in U.S. patent application Ser. No. 12/345,937 filed Dec. 30, 2008 and incorporated herein by reference, in particular, FIGS. 4-6 and the accompanying description, such as paragraphs [0051]-[0061] in the application as filed. The bone cement injector system can include first and second hydraulic assemblies 610A and 610B together with a controller and energy source in a single integrated station or box 605. In use, the first and second hydraulic assemblies 610A and 610B can allow for rapid switching between cement syringes in cases where multiple syringes of cement are injected. In a conventional hydraulic unit, it may require from 20 seconds to 2 minutes to retract a screw-driven mechanical drive mechanism that moves within a hydraulic cylinder. Thus, by providing two hydraulic assemblies, the flexibility of the system can be increased and the time required for a surgical procedure can be reduced.

System 600 of FIG. 15 can include an integrated station or control box 605 for use with the injectors as also described in U.S. patent application Ser. No. 12/345,937. As shown, a negative pressure source 320 and controller 325 can be built into the hydraulic controller box 605. The negative pressure source 320 is configured to receive at least one cement-carrying member or syringe 212 as in FIG. 3 for vacuum saturation of the polymer powder 105.

Figure 16:
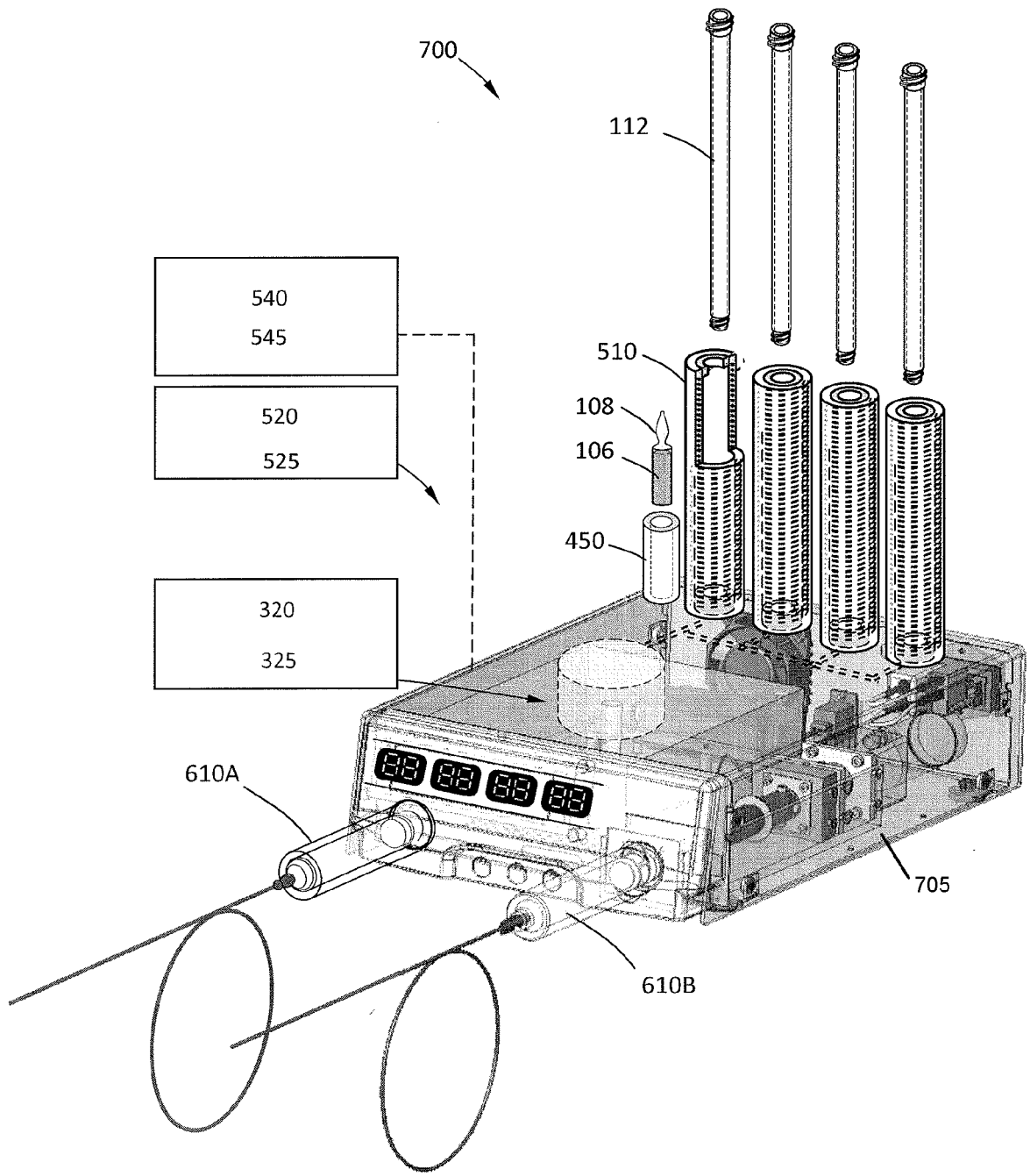
FIG. 16 is another embodiment of a cement injector system with first and second hydraulic assemblies, built-in vacuum saturation components, and a thermal management system.

FIG. 16 illustrates a system 700 for use with the a plurality of cement-carrying sleeves 112 as in FIG. 14, and includes first and second hydraulic assemblies 610A and 610B together with a controller, and thermal management system of FIG. 14 all integrated into a single unit 705. In all other respects, the integrated system 700 of FIG. 14 operates as described previously.

In some embodiments, the systems utilize computer algorithms that allow for temperature management of cement parameters to allow for selection of different cement viscosities across the different cement-carrying sleeves 112 by simple selection and actuation of a button. For example, higher and lower viscosities can be selected on demand.

In another embodiment, the hydraulic injection system can use a gel, such as a hydraulic fluid, which prevents loss or leakage of fluid during storage, shipping, sterilization and the like.

The above description is intended to be illustrative and not exhaustive. In addition, particular characteristics, features, dimensions and the like are presented in the dependent claims. These can be combined in various embodiments and fall within the scope of the disclosure. It should be understood that various additional embodiments encompass the dependent claims as if they were alternatively written in a multiple dependent claim format with reference to other independent claims. Specific characteristics and features of the embodiments of the systems and methods are described in relation to some figures and not in others, and this is for convenience only. While certain principles have been made clear in the exemplary descriptions and combinations, it will be obvious to those skilled in the art that modifications may be utilized in practice which are particularly adapted to specific environments and operative requirements without departing from the principles espoused herein.

Of course, the foregoing description is that of certain features, aspects and advantages, to which various changes and modifications can be made without departing from the spirit and scope of the disclosure. Moreover, the bone treatment systems and methods need not feature all of the objects, advantages, features and aspects discussed above. Thus, for example, those skill in the art will recognize that the systems and methods can be embodied or carried out in a manner that achieves or optimizes one advantage or a group of advantages as taught herein without necessarily achieving other objects or advantages as may be taught or suggested herein. In addition, while a number of variations have been shown and described in detail, other modifications and methods of use, which are within the scope of the disclosure, will be readily apparent to those of skill in the art based upon this disclosure. It is contemplated that various combinations or subcombinations of these specific features and aspects of embodiments may be made and still fall within the scope of the disclosure. Accordingly, it should be understood that various features and aspects of the disclosed embodiments can be combined with or substituted for one another in order to form varying modes of the discussed bone treatment systems and methods.

What is claimed is:

1. A system for preparing bone cement, comprising:
a base configured to couple to one or more elongate members, at least one of the elongate members configured to hold a non-liquid polymer component in a lumen thereof and configured to receive a liquid monomer component therein for saturation of the non-liquid polymer component by the liquid monomer component to form a curable bone cement; and
a negative pressure source configured for detachable communication with the base to draw the liquid monomer component into the non-liquid powder component;
one or more valves for selectively coupling the negative pressure source to particular elongate members of the plurality of elongate members;
a computer controller configured to control the plurality of valves, such that the valves can be opened or closed substantially simultaneously or a selected time intervals;
wherein the computer controller comprises a signal system to indicate to a user when to use a particular elongate member in a particular medical treatment or when to add liquid monomer component to a particular elongate member, and
wherein the base comprises one or more pathways that communicate with the lumen of the one or more elongate members and the negative pressure source.

2. The system of claim 1, further comprising a pressure regulator for regulating the pressure of the negative pressure source applied to draw the liquid polymer into the elongate member.

3. The system of claim 1, further comprising a funnel member for coupling to an end of the elongate members.

4. The system of claim 1, further comprising a cement ejection mechanism configured to couple to one of the elongate members and to eject bone cement from the elongated member into bone.

5. The system of claim 1, wherein the computer controller is operatively coupled to the negative pressure source for controlling a negative pressure level applied to each elongate member.

6. The system of claim 1, further comprising at least one of a heating and cooling mechanism for respectively heating or cooling the plurality of elongate members and the component or bone cement contained therein.

7. The system of claim 6, wherein the computer controller is configured to control either or both of the heating and cooling mechanisms.

8. A system for preparing bone cement, comprising:
a structure for receiving a plurality of bone cement preparation members, wherein the plurality of bone cement preparation members are configured to receive a liquid monomer component and a non-liquid polymer component, the combination of which forms a curable bone cement within the plurality of bone cement preparation members, the structure comprising:
a plurality of channels configured to connect an end of each of the plurality of bone cement preparation members to a negative pressure source; and
a plurality of temperature regulating assemblies, each assembly configured for heating or cooling one of the plurality of bone cement preparation members; and
a computer controller for controlling the amount of heat or cooling provided to the plurality of bone cement preparation members to heat or cool one of the components or the curable bone cement therein.

9. The system of claim 8, wherein each of the temperature regulating assemblies comprises a sleeve configured to receive and surround one of the plurality of bone cement preparation members.

10. The system of claim 9, wherein each of the temperature regulating assemblies is configured such that there is an air flow passage between an interior surface of the temperature regulating assembly and an exterior surface of the bone cement preparation member.

11. The system of claim 10, wherein each of the temperature regulating assemblies further comprises an input and an output port in fluid communication with the air flow passage and the system further comprises a heating or cooling source configured to generate a hot or cold flow of gas to enter the input port and exit the output port.

12. The system of claim 9, wherein each of the temperature regulating assemblies further comprises an inductive coil.

13. The system of claim 9, wherein each of the temperature regulating assemblies further comprises a seal configured to seal an access opening of the temperature regulating assembly once a bone cement preparation member has been placed inside the temperature regulating assembly.

14. The system of claim 8, further comprising a source of heat energy.

15. The system of claim 8, further comprising a liquid monomer heating assembly, configured for receiving, surrounding and heating a container of liquid monomer prior to combination with the polymer component.

16. The system of claim 8, wherein the structure further comprises a plurality of valves for selectively coupling the negative pressure source to particular bone cement preparation members.

17. The system of claim 8, further comprising the negative pressure source.

18. The system of claim 8, further comprising the plurality of bone cement preparation members.

19. The system of claim 8, further comprising a hydraulic computer control mechanism for injecting bone cement and first and second hydraulic drivers controlled by the computer control mechanism, wherein at least one bone cement preparation member is detachably coupleable to a hydraulic driver.

* * * * *